(12) United States Patent  
Perlman et al.

(10) Patent No.: US 10,621,790 B2  
(45) Date of Patent: Apr. 14, 2020

(54) SYSTEMS AND METHODS FOR ANATOMICAL SHELL EDITING

(71) Applicant: Boston Scientific Scimed Inc., Maple Grove, MN (US)

(72) Inventors: Mordechai Perlman, Cambridge, MA (US); Daniel Klebanov, Arlington, MA (US); Ruslan R. Hristov, Lexington, MA (US); Leon Fay, Lexington, MA (US); Jonathan Allen, Medford, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 79 days.

(21) Appl. No.: 15/275,464

(22) Filed: Sep. 25, 2016

(65) Prior Publication Data

US 2017/0092014 A1 Mar. 30, 2017

Related U.S. Application Data

(60) Provisional application No. 62/233,347, filed on Sep. 26, 2015.

(51) Int. Cl.
*A61B 5/00* (2006.01)
*A61B 5/044* (2006.01)
(Continued)

(52) U.S. Cl.
CPC .............. *G06T 19/20* (2013.01); *G06T 15/04* (2013.01); *G06T 17/20* (2013.01); *G16H 50/50* (2018.01);
(Continued)

(58) Field of Classification Search
USPC ................................. 345/423, 419
See application file for complete search history.

(56) References Cited

U.S. PATENT DOCUMENTS

| | | | |
|---|---|---|---|
| 4,649,924 | A | 3/1987 | Taccardi |
| 4,674,518 | A | 6/1987 | Salo |

(Continued)

FOREIGN PATENT DOCUMENTS

| | | |
|---|---|---|
| CN | 1253761 A | 5/2000 |
| CN | 101933803 A | 1/2011 |

(Continued)

OTHER PUBLICATIONS

International Search Report and Written Opinion issued in PCT/US2016/053613, dated Jan. 4, 2017, 11 pages.

(Continued)

*Primary Examiner* — Sing-Wai Wu
(74) *Attorney, Agent, or Firm* — Faegre Drinker Biddle & Reath LLP

(57) ABSTRACT

A system and method for voltage-guided anatomical shell editing includes outputting, to a display device, an anatomical shell of a cardiac structure. The anatomical shell is based on signals sensed by a mapping probe, each signal including a respective sensed voltage. User input specifying a first target depth for editing is received, as is a selection of a first region of the anatomical shell. A modified anatomical shell is generated by removing a first portion of the anatomical shell including the selected first region to a first editing depth based on the first target depth and generating a new surface region on the modified anatomical shell. Based on the voltage associated with the new surface region, the edit can be maintained, undone, and/or modified.

12 Claims, 11 Drawing Sheets

(51) Int. Cl.
  *G06T 15/04* (2011.01)
  *G06T 17/20* (2006.01)
  *G06T 19/20* (2011.01)
  *G16H 50/50* (2018.01)
  *G06F 3/0482* (2013.01)
  *A61B 5/0408* (2006.01)
  *G16H 30/40* (2018.01)

(52) U.S. Cl.
  CPC ............ *A61B 5/044* (2013.01); *A61B 5/0408* (2013.01); *A61B 5/6852* (2013.01); *A61B 5/6858* (2013.01); *A61B 5/6869* (2013.01); *A61B 2576/023* (2013.01); *G06F 3/0482* (2013.01); *G06T 2207/30048* (2013.01); *G06T 2210/41* (2013.01); *G06T 2219/2021* (2013.01); *G16H 30/40* (2018.01)

(56) References Cited

U.S. PATENT DOCUMENTS

| | | |
|---|---|---|
| 4,840,182 A | 6/1989 | Carlson |
| 4,920,490 A | 4/1990 | Isaacson |
| 5,156,151 A | 10/1992 | Imran |
| 5,284,142 A | 2/1994 | Goble et al. |
| 5,297,549 A | 3/1994 | Beatty et al. |
| 5,300,068 A | 4/1994 | Rosar et al. |
| 5,341,807 A | 8/1994 | Nardella |
| 5,381,333 A | 1/1995 | Isaacson et al. |
| 5,469,858 A | 11/1995 | Osborne |
| 5,480,422 A | 1/1996 | Ben-Haim |
| 5,483,968 A | 1/1996 | Adam et al. |
| 5,500,011 A | 3/1996 | Desai |
| 5,553,611 A | 9/1996 | Budd et al. |
| 5,568,809 A | 10/1996 | Ben-Haim |
| 5,577,502 A | 11/1996 | Darrow et al. |
| 5,588,429 A | 12/1996 | Isaacson et al. |
| 5,623,583 A | 4/1997 | Nishino |
| 5,634,469 A | 6/1997 | Bruder et al. |
| 5,647,870 A | 7/1997 | Kordis et al. |
| 5,662,108 A | 9/1997 | Budd et al. |
| 5,687,737 A | 11/1997 | Branham et al. |
| 5,697,377 A | 12/1997 | Wittkampf |
| 5,704,365 A | 1/1998 | Albrecht et al. |
| 5,722,402 A | 3/1998 | Swanson et al. |
| 5,810,740 A | 9/1998 | Paisner |
| 5,840,025 A | 11/1998 | Ben-Haim |
| 5,840,031 A | 11/1998 | Crowley |
| 5,846,198 A | 12/1998 | Killmann |
| 5,848,972 A | 12/1998 | Triedman et al. |
| 5,876,336 A | 3/1999 | Swanson et al. |
| 5,921,982 A | 7/1999 | Lesh et al. |
| 5,954,665 A | 9/1999 | Ben-Haim |
| 5,971,933 A | 10/1999 | Gopakumaran et al. |
| 5,983,126 A | 11/1999 | Wittkampf |
| 6,014,581 A | 1/2000 | Whayne et al. |
| 6,050,267 A | 4/2000 | Nardella et al. |
| 6,070,094 A | 5/2000 | Swanson et al. |
| 6,095,150 A | 8/2000 | Panescu et al. |
| 6,167,296 A | 12/2000 | Shahidi |
| 6,216,027 B1 | 4/2001 | Willis et al. |
| 6,226,542 B1 | 5/2001 | Reisfeld |
| 6,233,491 B1 | 5/2001 | Kordis et al. |
| 6,236,886 B1 | 5/2001 | Cherepenin et al. |
| 6,240,307 B1 | 5/2001 | Beatty et al. |
| 6,246,898 B1 | 6/2001 | Vesely et al. |
| 6,254,536 B1 | 7/2001 | DeVito |
| 6,278,894 B1 | 8/2001 | Salo et al. |
| 6,298,257 B1 | 10/2001 | Hall et al. |
| 6,301,496 B1 | 10/2001 | Reisfeld |
| 6,308,093 B1 | 10/2001 | Armoundas et al. |
| 6,314,310 B1 | 11/2001 | Ben-Haim et al. |
| 6,317,619 B1 | 11/2001 | Boernert et al. |
| 6,318,375 B1 | 11/2001 | Plicchi et al. |
| 6,360,123 B1 | 3/2002 | Kimchi et al. |
| 6,368,285 B1 | 4/2002 | Osadchy et al. |
| 6,400,981 B1 | 6/2002 | Govari |
| 6,490,474 B1 | 12/2002 | Willis et al. |
| 6,516,807 B1 | 2/2003 | Panescu et al. |
| 6,547,082 B1 | 4/2003 | Babini |
| 6,556,695 B1 | 4/2003 | Packer et al. |
| 6,574,492 B1 | 6/2003 | Ben-Haim et al. |
| 6,574,498 B1 | 6/2003 | Gilboa |
| 6,593,884 B1 | 7/2003 | Gilboa et al. |
| 6,600,948 B2 | 7/2003 | Ben-Haim et al. |
| 6,603,996 B1 | 8/2003 | Beatty et al. |
| 6,631,290 B1 | 10/2003 | Guck et al. |
| 6,640,119 B1 | 10/2003 | Budd et al. |
| 6,650,927 B1 | 11/2003 | Keidar |
| 6,690,963 B2 | 2/2004 | Ben-Haim et al. |
| 6,701,176 B1 | 3/2004 | Halperin et al. |
| 6,728,562 B1 | 4/2004 | Budd et al. |
| 6,735,465 B2 | 5/2004 | Panescu |
| 6,773,402 B2 | 8/2004 | Govari et al. |
| 6,807,439 B2 | 10/2004 | Edwards et al. |
| 6,839,588 B1 | 1/2005 | Rudy |
| 6,847,839 B2 | 1/2005 | Ciaccio et al. |
| 6,872,428 B2 | 3/2005 | Yang et al. |
| 6,892,090 B2 | 5/2005 | Verard et al. |
| 6,892,091 B1 | 5/2005 | Ben-Haim et al. |
| 6,893,588 B2 | 5/2005 | Lawson et al. |
| 6,939,309 B1 | 9/2005 | Beatty et al. |
| 6,941,166 B2 | 9/2005 | MacAdam et al. |
| 6,957,101 B2 | 10/2005 | Porath et al. |
| 6,978,168 B2 | 12/2005 | Beatty et al. |
| 6,984,207 B1 | 1/2006 | Sullivan et al. |
| 6,990,370 B1 | 1/2006 | Beatty et al. |
| 7,016,719 B2 | 3/2006 | Rudy et al. |
| 7,043,292 B2 | 5/2006 | Tarjan et al. |
| 7,136,694 B2 | 11/2006 | Hadley et al. |
| 7,263,397 B2 | 8/2007 | Hauck et al. |
| 7,505,810 B2 | 3/2009 | Harlev et al. |
| 7,515,954 B2 | 4/2009 | Harlev et al. |
| 7,628,757 B1 | 12/2009 | Koh |
| 7,629,981 B1 | 12/2009 | West |
| 7,729,752 B2 | 6/2010 | Harlev et al. |
| 7,890,155 B2 | 2/2011 | Burns et al. |
| 8,103,338 B2 | 1/2012 | Harlev et al. |
| 8,137,343 B2 | 3/2012 | Harlev et al. |
| 8,208,991 B2 | 6/2012 | Markowitz et al. |
| 8,463,368 B2 | 6/2013 | Harlev et al. |
| 8,498,699 B2 | 7/2013 | Wells et al. |
| 8,571,647 B2 | 10/2013 | Harlev et al. |
| 8,744,566 B2 | 6/2014 | Harlev et al. |
| 8,768,440 B1 | 7/2014 | Brodnick et al. |
| 9,113,809 B2 | 8/2015 | Harlev et al. |
| 9,510,769 B2 | 12/2016 | Harlev et al. |
| 9,636,032 B2 | 5/2017 | Thakur et al. |
| 9,898,825 B2* | 2/2018 | Rivet-Sabourin ............ G01R 33/5608 |
| 9,918,649 B2 | 3/2018 | Thakur et al. |
| 2002/0065459 A1 | 5/2002 | MacAdam et al. |
| 2002/0151807 A1 | 10/2002 | Goldin |
| 2003/0018251 A1 | 1/2003 | Solomon |
| 2003/0065271 A1 | 4/2003 | Khoury |
| 2003/0076277 A1 | 4/2003 | Muramatsu et al. |
| 2003/0078509 A1* | 4/2003 | Panescu ............ A61B 5/06 600/509 |
| 2003/0093067 A1 | 5/2003 | Panescu |
| 2003/0216630 A1 | 11/2003 | Jersey-Willuhn et al. |
| 2004/0059237 A1 | 3/2004 | Narayan et al. |
| 2004/0077942 A1 | 4/2004 | Hall et al. |
| 2004/0097806 A1 | 5/2004 | Hunter et al. |
| 2004/0158165 A1 | 8/2004 | Yonce et al. |
| 2004/0243015 A1 | 12/2004 | Smith et al. |
| 2004/0254437 A1 | 12/2004 | Hauck et al. |
| 2005/0037489 A1 | 2/2005 | Gepstein et al. |
| 2005/0038337 A1 | 2/2005 | Edwards |
| 2005/0054918 A1 | 3/2005 | Sra |
| 2005/0107834 A1 | 5/2005 | Freeman et al. |
| 2005/0154282 A1 | 7/2005 | Li et al. |
| 2005/0288599 A1 | 12/2005 | MacAdam et al. |
| 2006/0085049 A1* | 4/2006 | Cory ............ A61B 5/0536 607/48 |

(56) References Cited

U.S. PATENT DOCUMENTS

| | | |
|---|---|---|
| 2006/0106375 A1 | 5/2006 | Werneth et al. |
| 2006/0116575 A1 | 6/2006 | Willis |
| 2006/0122526 A1 | 6/2006 | Berenfeld et al. |
| 2006/0173251 A1 | 8/2006 | Govari et al. |
| 2006/0178587 A1 | 8/2006 | Khoury |
| 2006/0241401 A1 | 10/2006 | Govari et al. |
| 2007/0016007 A1 | 1/2007 | Govari et al. |
| 2007/0038078 A1 | 2/2007 | Osadchy |
| 2007/0049821 A1 | 3/2007 | Willis |
| 2007/0112276 A1 | 5/2007 | Simms |
| 2007/0197929 A1 | 8/2007 | Porath et al. |
| 2007/0232949 A1 | 10/2007 | Saksena |
| 2007/0255588 A1 | 11/2007 | Hamilton |
| 2007/0265539 A1 | 11/2007 | Hastings et al. |
| 2007/0270688 A1 | 11/2007 | Gelbart et al. |
| 2007/0270703 A1 | 11/2007 | He et al. |
| 2007/0287902 A1 | 12/2007 | Fuimaono et al. |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0137934 A1 | 6/2008 | Sakaguchi et al. |
| 2008/0188765 A1 | 8/2008 | Stolarski et al. |
| 2008/0190438 A1 | 8/2008 | Harlev et al. |
| 2008/0221566 A1 | 9/2008 | Krishnan |
| 2008/0222109 A1 | 9/2008 | Sakurai |
| 2008/0234588 A1 | 9/2008 | Feldman et al. |
| 2008/0249424 A1 | 10/2008 | Harlev et al. |
| 2008/0269813 A1 | 10/2008 | Greenhut et al. |
| 2008/0273227 A1 | 11/2008 | Dattilo et al. |
| 2009/0103793 A1 | 4/2009 | Borland et al. |
| 2009/0171274 A1 | 7/2009 | Harlev et al. |
| 2009/0177072 A1 | 7/2009 | Harlev et al. |
| 2009/0253976 A1 | 10/2009 | Harlev et al. |
| 2009/0262979 A1* | 10/2009 | Markowitz .......... A61B 5/0422 382/103 |
| 2009/0264741 A1* | 10/2009 | Markowitz .......... A61B 5/0422 600/424 |
| 2009/0264777 A1* | 10/2009 | Markowitz .......... A61B 5/0422 600/506 |
| 2010/0023082 A1 | 1/2010 | Dong et al. |
| 2010/0094274 A1 | 4/2010 | Narayan et al. |
| 2010/0268059 A1* | 10/2010 | Ryu .................. A61B 5/042 600/407 |
| 2010/0286551 A1 | 11/2010 | Harlev et al. |
| 2011/0098771 A1 | 4/2011 | Thakur et al. |
| 2011/0169828 A1* | 7/2011 | Pedersen .............. G06T 17/20 345/423 |
| 2011/0206256 A1 | 8/2011 | Ramanathan et al. |
| 2011/0251505 A1 | 10/2011 | Narayan et al. |
| 2011/0288605 A1 | 11/2011 | Kaib et al. |
| 2012/0029504 A1 | 2/2012 | Afonso et al. |
| 2012/0184858 A1 | 7/2012 | Harlev et al. |
| 2012/0184863 A1 | 7/2012 | Harlev et al. |
| 2012/0184865 A1 | 7/2012 | Harlev et al. |
| 2012/0191087 A1 | 7/2012 | Pachon Mateos et al. |
| 2012/0226110 A1* | 9/2012 | Markowitz .......... A61B 5/0422 600/301 |
| 2012/0290976 A1 | 11/2012 | Lahm et al. |
| 2013/0035576 A1 | 2/2013 | O'Grady et al. |
| 2013/0079645 A1 | 3/2013 | Amirana et al. |
| 2013/0274582 A1* | 10/2013 | Afonso ................ A61B 5/0422 600/374 |
| 2013/0310702 A1 | 11/2013 | Reinders et al. |
| 2014/0052118 A1 | 2/2014 | Laske et al. |
| 2014/0073194 A1 | 3/2014 | Lim et al. |
| 2014/0200874 A1 | 7/2014 | Zeng et al. |
| 2014/0235986 A1 | 8/2014 | Harlev et al. |
| 2014/0278324 A1 | 9/2014 | Bates et al. |
| 2014/0330150 A1 | 11/2014 | Thakur et al. |
| 2014/0343388 A1 | 11/2014 | Thakur et al. |
| 2015/0133764 A1 | 5/2015 | Sakuragi |
| 2015/0254419 A1 | 9/2015 | Laughner et al. |
| 2015/0254893 A1 | 9/2015 | Laughner et al. |
| 2015/0373068 A1 | 12/2015 | Allen et al. |
| 2016/0012646 A1* | 1/2016 | Huang .................. G06T 5/005 345/419 |
| 2016/0051204 A1 | 2/2016 | Harlev et al. |
| 2016/0066814 A1* | 3/2016 | Markowitz .......... A61B 5/0422 600/424 |
| 2016/0100770 A1* | 4/2016 | Afonso ................ A61B 5/0422 600/515 |
| 2017/0024907 A1* | 1/2017 | Bermano ........... G06K 9/00604 |
| 2017/0164928 A1 | 6/2017 | Oh et al. |
| 2017/0189118 A1* | 7/2017 | Chopra .................. A61B 34/30 |
| 2017/0278301 A1 | 9/2017 | Peterson et al. |
| 2017/0311833 A1* | 11/2017 | Afonso ................ A61B 5/0422 |
| 2018/0153426 A1 | 6/2018 | Thakur et al. |

FOREIGN PATENT DOCUMENTS

| | | |
|---|---|---|
| CN | 102821694 A | 12/2012 |
| CN | 102917638 A | 2/2013 |
| EP | 2204120 A1 | 7/2010 |
| EP | 2427106 A | 3/2012 |
| EP | 2485194 A2 | 8/2012 |
| JP | 2010057943 A | 3/2010 |
| WO | 1999005971 A1 | 2/1999 |
| WO | WO2006037172 A1 | 4/2006 |
| WO | 2006066324 A1 | 6/2006 |
| WO | 2007035306 A2 | 3/2007 |
| WO | 2007108776 A2 | 9/2007 |
| WO | 2007146864 A3 | 12/2007 |
| WO | 2008138009 A1 | 11/2008 |
| WO | 2010054320 A1 | 5/2010 |
| WO | 2010129095 A2 | 11/2010 |
| WO | WO2012037471 A2 | 3/2012 |
| WO | 2012092016 A1 | 7/2012 |
| WO | 2013006713 A2 | 1/2013 |
| WO | 2014185977 A1 | 11/2014 |
| WO | 2015130824 A1 | 9/2015 |
| WO | 2015134248 A1 | 9/2015 |

OTHER PUBLICATIONS

International Search Report and Written Opinion issued in PCT/US2015/017289, dated May 6, 2015, 10 pages.
International Search Report and Written Opinion issued in PCT/US2015/017482, dated Jun. 5, 2015, 9 pages.
Jain et al., "Cell Therapy Attenuates Deleterious Ventricular Remodeling and Improves Cardiac Performance after Myocardial infarction", Circulation, 103:1920-1927, 2001.
Jalife, "Rotors and Spiral Waves in Atrial Fibrillation", Journal of Cardiovascular Electrophysiology, 14:776-780, 2003.
Jane et al., "Alignment Methods for Averaging of High-Resolution Cardiac Signals: A Comparative Study of Performance", IEEE Transactions on Biomedical Engineering, 38(6):571-579, 1991.
Japanese Office Action in JP Application No. 2009-515586, dated Jun. 26, 2012, 4 pages.
Jia et al., "Electrophysiologic Endocardial Mapping from a Noncontact Nonexpandable Catheter: A Validation Study of a Geometry-Based Concept". Journal of Cardiovascular Electrophysiology, 11:1238-1251, 2000.
Kikuchi et al., "Targeted Modification of Atrial Electrophysiology by Homogeneous Transmural Atrial Gene Transfer", Circulation, 111:264-270, 2005.
Kistler et al., "Validation of Three-Dimensional Cardiac Image Integration: Use of Integrated CT Image into Electroanatomic Mapping System to Performa Catheter Ablation of Atrial Fibrillation", Journal of Cardiovascular Electrophysiology, 17:341-348, 2006.
Kuklik et al., "The reconstruction, from a set of points, and analysis of the interior surface of the heart chamber", Physiol. Meas. 25:617-627, 2004.
Kun, Stevan et al., "Conductance Volumetric Model of an Eccentrically Positioned Catheter Wthin a Three-Compartment Ellipsoidal Ventricle", IEEE Transactions on Biomedical Engineering, vol. 40, No. 6, Jun. 1993, pp. 589-592.
L. Piegl, W. Tiller: The NURBS Book, 2nd Edition, Monographs in Visual Communication, Springer (1997).

(56) References Cited

OTHER PUBLICATIONS

Laciar et al., Improved Alignment Method for Noisy High-Resolution ECG and Holter Records Using a Multiscale Cross-Correlation, IEEE Transactions on Biomedical Engineering, 50(3), pp. 344-353, 2003.
Liu et al., "Endocardial Potential Mapping from a Noncontact Nonexpandable Catheter: A Feasibility Study", Annals of Biomedical Engineering, 26:994-1009, 1998.
Lorensen et al. "Marching Cubes: A High Resolution 3D Surface Construction Algorithm", Computer Graphics, 21(4):163-169, Jul. 1987.
Makela et al., "A Review of Cardiac Image Registration Methods", IEEE Transactions on Medical Imaging, 21(9):1011-1021, Sep. 2002.
Malladi, R. et al., "A Geometric Approach to Segmentation and Analysis of 3D Medical Images", Mathematical Methods in Biomedical Image Analysis, Proceedings of the Workshop on, Jun. 21-22, 1996, pp. 244-252.
Mangan, Alan et al., "Partitioning 3D Surface Meshes Using Watershed Segmentation", IEEE Transactions on Visualization and Computer Graphics, vol. 05, No. 4, pp. 308-321, (Oct.-Dec. 1999).
Meininger et al., "Initial Experience with a Novel Focused Ultrasound Ablation System for Ring Ablation Outside the Pulmonary Vein", Journal of Interventional Cardiac Electrophysiology, 8:141-148, 2003.
Merrill, Daniel R. et al., "Electrical stimulation of excitable tissue: design of efficacious and safe protocols", Journal of Neuroscience Methods, vol. 141, pp. 171-198 (2005).
Miller, "Editor's Forum—Application of Registration for Ablation: A Marriage of Technologies", Journal of Interventional Cardiac Electrophysiology, 11:87-89, 2004.
Nademanee et al., "A New Approach for Catheter Ablation of Atrial Fibrillation: Mapping of the Electrophysiologic Substrate", Journal of the American College of Cardiology, 43(11):2044-2053, 2004.
Non-final Office Action issued in U.S. Appl. No. 11/451,898, dated Sep. 25, 2008, 13 pages.
Non-final Office Action issued in U.S. Appl. No. 11/451,908, dated Sep. 4, 2008, 12 pages.
Noseworthy et al., "The Impact of Respiration on Left Atrial and Pulmonary Venous Anatomy: Implications for Image-Guided Intervention", Heart Rhythm, 2(11), pp. 1173-1178, Nov. 2005.
Pappone et al., "Robotic Magnetic Navigation for Atrial Fibrillation Ablation", Journal of the American College of Cardiology, 47(7):1390-1400, 2006.
Paragios, "A Level Set Approach for Shape-Driven Segmentation and Tracking of the Left Ventricle", IEEE Transactions on Medical Imaging, 22(6):773-776, Jun. 2003.
Persson et al., "A Simple Mesh Generator in MATLAB", SIAM Review, 46(2):329-345, 2004.
Persson, "Mesh Generation for implicit Geometries", Massachusetts Institute of Technology—Thesis, Feb. 2005.
Pham, Dzung et al., "Current Methods in Medical image Segmentation", Annu. Rev. Biomed. Eng., 02: pp. 315-337, (2000).
Rao et al., "Novel Noncontact Catheter System for Endocardial Electrical and Anatomical Imaging", Annals of Biomedical Engineering, 32(4):573-584, 2004.
Reddy et al., "Integration of Cardiac Magnetic Resonance Imaging With Three-Dimensional Electroanatornic Mapping to Guide Left Ventricular Catheter Manipulation—Feasibility in a Porcine Model of Healed Myocardial Infarction", Journal of the American College of Cardiology, 44(11):2202-2213, 2004.
Reddy et al., "Use of a Diode Laser Balloon Ablation Catheter to Generate Circumferential Pulmonary Venous Lesions in an Open-Thoracotomy Caprine Model", PACE, 27:52-57, 2004.
Sanders et al., "Spectral Analysis Identifies Sites of High-Frequency Activity Maintaining Atrial Fibrillation in Humans", Circulation, 112:789-797, 2005.
Sethian, "Level Set Methods arid Fast Marching Methods: Evolving Interfaces in Computational Geometry, Fluid Mechanics, Computer Vision, and Materials Science", Department of Mathematics-University of California, Berkeley, Cambridge University Press, 1999.
Simon et al., "Electroanatomic Mapping of the Right Atrium With a Right Atrial Basket Catheter and Three-Dimensional Intracardiac Echocardiography", PACE, 27:318-326, 2004.
Smits et al., "Catheter-Based Intramyocarial Injection of Autologous Skeletal Myoblasts as a Primary Treatment of Ischemic Heart Failure", Journal of the American College of Cardiology, 42(12):2063-2069, 2003.
Solomon et al., "Real-Time Cardiac Catheter Navigation on Three-Dimensional CT Images", Journal of Interventional Cardiac Electrophysiology, 8:27-36, 2003.
Sra et al., "Registration of Three-Dimensional Left Atrial Computed Tomographic Images With Projection Images Obtained Using Fluoroscopy", Circulation, 112:3763-3768, 2005.
Sra, Jasbir et al, "Registration of 3D Computed Tomographic Images With Interventional Systems: Implications for Catheter Ablation of Atrial Fibrillation", J Interv Card Electrophysiol, 16:141-148, 2006.
Stevenson, "Radiofrequency Catheter Ablation of Ventricular Tachycardia After Myocardial Infarction", Circulation, 98:308-314, 1998.
Supplemental European Search Report issued in EP App[lication 10772414.8, dated May 7, 2013, 6 pages.
Supplemental European Search Report issued in EP Application No. 09824015, dated Jun. 1, 2012, 7 pages.
Supplementary European Search Report issued in EP Applicaion No. 09727423, dated May 15, 2012, 5 pages.
Supplementary European Search Report issued in EP Application No. 07798369.0 dated Jul. 30, 2010, 6 pages.
Supplementary Europeant Search Report issued in EP Application No. 08728501, dated Feb. 25, 2011, 4 pages.
Taccardi et al., "A New Intracavitary Probe for Detecting the Site of the Origin of Ectopic Ventricular Beats During One Cardiac Cycle", Circulation, 75(1):272-281, 1987.
Thai et al., "Novel Applications in Catheter Ablation", Journal of Interventional Cardiac Electrophysiology, 13:17-21, 2005.
Thiagalingam et al., "Noncontact Mapping of the Left Ventricle: Insights from Validation Wth Transmural Contact Mapping", PACE, 27:570-578, 2004.
Voth, "The Inverse Problem of Electrocardiography: Industrial Solutions and Simulations", BEM and NFSI Conference Proceedings, Minneapolis, MN, May 12-15, 2005, pp. 191-194.
Wittkampf et al., "LocaLisa: New Technique for Real-Time 3-Dimensional Localization of Regular Intracardiac Electrodes", Circulation, 99:1312-1317, 1999.
Yezzi, Anthony et al., "A Geometric Snake Model for Segmentation of Medical Imagery", IEEE Transactions on Medical Imag, vol. 16, No. 2, Apr. 1997.
Adams et al., "Seeded Region Growing", IEEE Transactions on Pattern Analysis and Machine Intelligence, 16(6):641-647, 1994.
Arthur et al., "Clinical Use of Intracardiac Impedance: Current Applications and Future Perspectives", PACE, vol. 24, No. 4, Part 1, Apr. 2001, pp. 500-506.
Baan, Jan et al., "Continuous Measurement of Left Ventricular Volume in Animals and Humans by Conductance Catheter", Diagnostic Methods-Conductance Catheter, Circulation, vol. 70, No. 5, 1984, pp. 812-823.
Badics et al., "Real-Time Reconstruction of Endocardial Potential Maps in Non-Contact Cardiac Mapping", International Journal for computation and Mathematics in Electrical and Electronic Engineering (COMPEL), vol. 28, No. 4, 2009.
Ben-Haim et al., "Nonfluoroscopic, in Vivo Navigation and Mapping Technology", Nature Medicine, 2(12):1393-1395, Dec. 1996.
Besl et al., "A Method for Registration of 3-D Shapes", IEEE Transactions on Pattern Analysis and Machine Intelligence, 14(2):239-256, Feb. 1992.
Blomstrom-Lundqvist et al., "ACC/AHA/ESC Guidelines for the Management of Patients With Supraventricular Arrhythmias-Executive Summary", Journal of the American College of Cardiology, 42(8):1493-1531, 2003.

(56) References Cited

OTHER PUBLICATIONS

Breithardt et al., "AHA Medical/Scientific Statement—Special Report: Standards for Analysis of Ventricular Late Potentials Using High-Resolution or Signal-Averaged Electrocardiography", Circulation, 83(4):1481-1488, Apr. 1991.
Brooks et al., "Electrical Imaging of the Heart", IEEE Signal Processing Magazine, pp. 24-42, 1997.
Buneo, Christopher A., Analyzing Neural Responses with Vector Fields, Journal of Neuroscience Methods, vol. 197, 2011, pp. 109-117.
Caspi et al., "Stem Cell Research: Regenerating the Heart Using Human Embryonic Stem Cells—from Cell to Bedside", IMAJ 8:208-214, 2006.
Cheney et al., "Electrical Impedance Tomography", SIAM Review 41(1):85-101, 1999.
Communication pursuant to Article 94(3) EPC issued in EP Application No. 07 798 369.0, dated Nov. 17, 2011, 5 pages
De Groot et al., "Three-Dimensional Catheter Positioning During Radiofrequency Ablation in Patients: First Application of a Real-Time Position Management System", Journal of Cardiovascular Electrophysiology, 11(11):1183-1192, Nov. 2000.
Donahue et al., "Focal Modification of Electrical Conduction in the Heart by Viral Gene Transfer", Nature Medicine, 6(12):1395-1398, 2000.
Dong et al., "Integrated Electroanatomic Mapping With Three-Dimensional Computed Tomographic Images for Real-Time Guided Ablations", Circulation 113:186-194, 2006.
Durrer et al., "Total Excitation of the Isolated Human Heart", Circulation, vol. XLI, pp. 899-912, 1970.
E. J. Haug et al.: Design Sensitivity Analysis of Structural Systems, Mathematics in Science and Engineering, vol. 177 (1986).
Ector et al., "Cardiac Three-Dimensional Magnetic Resonance Imaging and Fluoroscopy Merging—A New Approach for Electroanatornic Mapping to Assist Catheter Ablation", Circulation, (Dec. 13, 2005), pp. 3769-3776.
Extended European Search Report issued in EP Application No. 10 772 414, dated May 7, 2013, 6 pages.
Fletcher, R. "Chapter 6: Sums of Squares and Nonlinear Equations," Practical Methods of Optimization, 2nd Edition, J. Willey & Sons, pp. 110-119 (1967).
Friedman, "Catheter Cryoablation of Cardiac Arrhythmias", Current Opinion in Cardiology, 20:48-54, 2005.
Friedman, "Novel Mapping Techniques for Cardiac Electrophysiology", Heart 2002, 87:575-582.
Geddes, L.A. et al., "Criteria for the Selection of Materials for Implanted Electrodes", Annals of Biomedical Engineering, vol. 31, pp. 879-890 (2003).
Gepstein et al., "A Novel Method for Nonfluoroscopic Catheter-Based Electroanatomical Mapping of the Heart", Circulation 95:1611-1622, 1997.
Gitosusastro et al., Performance Derivative Calculations and Optimization Process, IEEE Transactions on Magnetics, vol. 25, No. 4 (Jul. 1989) pp. 2834-2839.
Hansen: Rank-Deficient and Discrete Ill-Posed Problems: Numerical Aspects of Linear Inversion, SIAM, Philadelphia, USA, pp. 100-103, 1998.
He, Ye H. et al., "An Interactive Graphical System for Automated Mapping and Display of Cardiac Rhythms", Journal of Electrocardiology, vol. 32, No. 3, 1999, 17 pages.
He, Ye H., "An interactive graphical system for automated mapping and display of cardiac rhythms", Journal of Electrocardiology, vol. 32, No. 3, Jul. 1, 1999, pp. 225-241.
Holm, Magnus et al. A New Method for Analysis of Atrial Activation During Chronic Atrial Fibrillation in Man. IEEE Transactions on Biomedical Engineering, 43(2): 198-210, Feb. 1996.

Huang, Yi-Chih et al., "Development of a Third Generation Intraventricuiar Impedance Imaging (III) System: Evaluation of Hardware Design", Engineering in Medicine and Biology Society,. Proceedings of the 19th Annual International Conference of the IEEE, Oct. 30-Nov. 2, 1997 vol. 6, pp. 336-338 (1997).
International Preliminary Report on Patentability in PCT/US2007/070854, dated Dec. 16, 2008, 9 pages.
International Preliminary Report on Patentability in PCT/US2009/061277, dated May 3, 2011 11 pages.
International Preliminary Report on Patentability in PCT/US2010/027568 dated Oct. 25, 2011, 4 pages.
International Preliminary Report on Patentability issued in PCT/US2008/052385 dated Aug. 11, 2009, 6 pages.
International Preliminary Report on Patentability issued in PCT/US2009/036099, dated Oct. 14, 2010, 20 pages.
International Preliminary Report on Patentability issued in PCT/US2010/027436, dated Nov. 9, 2011, 4 pages.
International Preliminary Report on Patentability issued in PCT/US2014/000114, dated Nov. 26, 2015, 9 pages.
International Preliminary Report on Patentability issued in PCT/US2014/036939, dated Nov. 19, 2015, 8 pages.
International Preliminary Report on Patentability issued in PCT/US2015/0017289 dated Sep. 15, 2016, 8 pages.
International Preliminary Report on Patentability issued in PCT/US2015/017482 dated Sep. 15, 2016, 4 pages.
International Search Report and the Written Opinion in PCT/US08/52385 dated Aug. 8, 2008, 11 pages.
International Search Report and Written Opinion in PCT/US2010/027568, dated Nov. 4, 2010, 6 pages.
International Search Report and Written Opinion in PCT/US2012/020946, dated May 7, 2012, 15 pages.
International Search Report and Written Opinion issued in PCT/US2007/070854, dated Sep. 12, 2008, 10 pages.
International Search Report and Written Opinion issued in PCT/US2009/036099, dated Apr. 28, 2009, 21 pages.
International Search Report and Written Opinion issued in PCT/US2009/061277, dated Apr. 8, 2010, 12 pages.
International Search Report and Written Opinion issued in PCT/US2010/027436 dated Oct. 27, 2010, 10 pages.
International Search Report and Written Opinion issued in PCT/US2014/000114, dated Sep. 8, 2014, 12 pages.
International Search Report and Written Opinion issued in PCT/US2014/036939, dated Jul. 30, 2014, 11 pages.
Andras Lasso et al., "SlicerWiki VolumeClip", Dec. 25, 2014, pp. 1-4, XP55332376, retrieved from teh internet: https://www.slicer.org/wiki/Documentation/4.4/Extensions/VolumeClip, retrieved on Jan. 5, 2017.
Anonymous: Solid Commands—Rhino 3-D Modeling (Rhinoceros 5), Sep. 17, 2015, XP055332631, Retrieved from Internet: http://docs.mcneel.com/rhino/5/help/en-us/seealso/sak_solidtools.htm, retrieved on Jan. 5, 2017, see under Cap, 2 pages.
International Search Report and Written Opinion issued in PCT/US2016/053633, dated Jan. 17, 2017, 14 pages.
International Search Report and Written Opinion issued in PCT/US2016/053630, dated Jan. 17, 2017, 12 pages.
International Preliminary Report on Patentability issued in PCT/US2016/053613, dated Apr. 5, 2018, 7 pages.
International Preliminary Report on Patentability issued in PCT/US2016/053630, dated Apr. 5, 2018, 7 pages.
International Preliminary Report on Patentability issued in PCT/US2016/053633, dated Apr. 5, 2018, 9 pages.
Diaz, J., Monclus, E., Navazo, I., and Vazquez, P. Adaptive cross-sections of anatomical models. Pacific Graphics, 31(7):2155-2164, 2012.
Wilmot, L., Ritter, L., Agrawala, M., Curless, B., and Salesin, D. Interactive cutaway illustration of complex 3D models. ACM Transactions on Graphics, 26(3):31-1-31-11, Jul. 2007.

* cited by examiner

SYSTEMS AND METHODS FOR ANATOMICAL SHELL EDITING

CROSS-REFERENCE TO RELATED APPLICATION

This application claims priority to Provisional Application No. 62/233,347, filed Sep. 26, 2015, which is herein incorporated by reference in its entirety.

TECHNICAL FIELD

The present disclosure generally relates to cardiac mapping systems and methods. More specifically, the present disclosure relates to editing anatomical shells that are based on cardiac structures.

BACKGROUND

Diagnosing and treating cardiac disorders often involve the introduction of a catheter into a cardiac chamber through the surrounding vasculature. The catheter has a plurality of sensors, located on the catheter's distal end. Information received from the plurality of sensors, including the position of the plurality of sensors and electrical signals associated with each position, can be used to generate and display an approximate anatomical shell of the cardiac chamber. In some instances, the anatomical shell can include representations of features of the electrical signals associated with each position. The anatomical shell can be used by a physician or other medical professional for treating cardiac disorders.

One consideration of anatomical shell construction is how close the shape of the anatomical shell is to the actual shape of the cardiac tissue. While anatomical shell construction using a catheter having a plurality of sensors may provide a fair approximation of the cardiac tissue, there often may be various issues associated with it. One issue is "under-contact," in which some points of the constructed anatomical shell are a significant distance from the actual tissue. Another issue is "over-contact," in which the catheter operator has exerted too much force during a portion of the reconstruction phase and pushes the cardiac tissue outwards resulting in shapes that constitute an exaggerate representation of the cardiac chamber. Even another issue is "webbing," in which small, sharp features of the cardiac chamber do not appear on the anatomical shell. This problem may be exacerbated by the catheter's rigidity.

SUMMARY

Embodiments of the subject matter disclosed herein include cardiac mapping systems that facilitate editing a constructed anatomical shell. In embodiments, a user-editing toolbox may include tools for selecting and removing specific sub-volumes, surface regions, and/or the like. In embodiments, a processing device may be configured to implement one or more algorithms to automatically edit the anatomical shell. In this manner, embodiments of the disclosure may facilitate enhancing the accuracy of cardiac mapping technologies. Exemplary embodiments include the following.

In an Example 1, a processor-implemented method for voltage-guided anatomical shell editing, the processor-based method comprising: outputting, to a display device, an anatomical shell of a cardiac structure, wherein the anatomical shell is based on a plurality of signals sensed by a mapping probe and wherein each of the plurality of signals includes a respective sensed voltage; receiving, from the user input device, a user input specifying a first target depth for editing; receiving, from a user input device, a selection of a first region of the anatomical shell; generating a first modified anatomical shell by: removing a first portion of the anatomical shell, the first portion of the anatomical shell comprising the selected first region of the surface and extending inward to a first editing depth based on the first target depth, the first editing depth comprising at least one finite depth, and generating a first new surface region on the first modified anatomical shell, corresponding to the selected region, wherein the first new surface is disposed at the first editing depth and includes at least one representation of a sensed voltage at the first editing depth; outputting, to the display device, the first modified anatomical shell.

In an Example 2, the method according to Example 1, further comprising: receiving, from the user input device, a command to undo the generation of the first modified anatomical shell; regenerating the anatomical shell; and outputting the regenerated anatomical shell to the display device.

In an Example 3, the method according to any of Examples 1 and 2, further comprising: receiving, from the user input device, a user input specifying a second target depth for editing; receiving, from a user input device, a selection of a second region of the anatomical shell, the second region comprising at least a portion of the first region; generating a second modified anatomical shell by: removing a second portion of the anatomical shell, the second portion of the anatomical shell comprising the selected second region of the surface and extending inward to a second editing depth based on the second target depth, the second editing depth comprising at least one finite depth, and generating a second new surface region on the second modified anatomical shell, corresponding to the selected second region, wherein the second new surface is disposed at the second editing depth and includes at least one representation of a sensed voltage at the second editing depth; and outputting, to the display device, the second modified anatomical shell.

In an Example 4, the method according to Example 3, wherein the second target depth is at least 1 millimeter and at most 5 millimeters.

In an Example 5, the method according to any of Examples 3-4, wherein the at least one representation of a sensed voltage at the first editing depth indicates a voltage magnitude corresponding to a blood pool.

In an Example 6, the method according to any of Examples 3-5, wherein the at least one representation of a sensed voltage at the second editing depth indicates a voltage magnitude corresponding to cardiac tissue.

In an Example 7, a processor-based method for anatomical shell editing comprises generating a first anatomical shell, wherein the first anatomical shell comprises a first surface that intersects a first plurality of mesh points, the first plurality of mesh points corresponding to a plurality of signals, wherein each of the plurality of signals includes at least one respective sensed electrical signal; selecting a test point, wherein the first surface does not intersect the test point, the test point having a position within a test neighborhood of a position of a first mesh point; performing a test associated with the test point, comprising: determining a first value of a metric corresponding to the first mesh point; determining a second value of the metric corresponding to the test point; computing a gradient feature of the metric based on the first and second values; determining whether the gradient feature satisfies a condition; and generating a second anatomical shell, wherein the second anatomical shell comprises a second surface that intersects a second plurality of mesh points, wherein: if the gradient feature satisfies the condition, the second plurality of mesh points includes the test point; and if the gradient feature does not satisfy the condition, the second plurality of mesh points does not include the test point.

In an Example 8, the method according to Example 7, wherein, if the gradient feature does not satisfy the condition, the method further comprises: selecting an additional test point, the additional test point having a position within the test neighborhood of the position of the first mesh points; and performing the test associated with the additional test point.

In an Example 9, the method according to any of Examples 7 and 8, wherein the position of the test point is located opposite the direction of a normal to the first surface at the first mesh point.

In an Example 10, the method according to any of Examples 7-9, wherein the test neighborhood comprises a sphere with a radius of 2 millimeters.

In an Example 11, the method according to any of Examples 7-10, wherein the metric comprises at least one of an out-of-cardiac-band impedance measurement, a unipolar electrode activation voltage measurement, a contact force measurement of the mapping probe, and a position-based cardiac motion measurement.

In an Example 12, the method according to any of Examples 7-11, wherein performing the test further comprises: determining a sensed voltage value corresponding to the test point; and determining whether the sensed voltage value exceeds a voltage threshold.

In an Example 13, the method according to Example 12, wherein: if the gradient feature satisfies the condition and the sensed voltage value exceeds the voltage threshold, the second plurality of mesh points includes the test point; and if the gradient feature does not satisfy the condition or the sensed voltage value does not exceed the voltage threshold, the second plurality of mesh points does not include the test point.

In an Example 14, the method according to any of Examples 7-13, wherein determining whether the gradient feature satisfies a condition comprises determining whether an absolute value of the gradient feature exceeds a gradient threshold.

In an Example 15, a system comprises: a mapping probe configured to sense a plurality of signals associated with a cardiac structure; a processing device configured to: generate a first anatomical shell, wherein the first anatomical shell comprises a first surface that intersects a first plurality of mesh points, the first plurality of mesh points corresponding to a plurality of signals, wherein each of the plurality of signals includes at least one respective sensed electrical signal; select a test point, wherein the first surface does not intersect the test point, the test point having a position within a test neighborhood of a position of a first mesh point; determine a first value of a metric corresponding to the first mesh point; determine a second value of the metric corresponding to the test point; compute a gradient feature of the metric based on the first and second values; determine whether the gradient feature satisfies a condition; and generate a second anatomical shell, wherein the second anatomical shell comprises a second surface that intersects a second plurality of mesh points; wherein if the gradient feature satisfies the condition, the second plurality of mesh points includes the test point, and if the gradient feature does not satisfy the condition, the second plurality of mesh points does not include the test point; and a display device configured to display the second anatomical shell.

In an Example 16, a processor-implemented method for voltage-guided anatomical shell editing comprises: outputting, to a display device, an anatomical shell of a cardiac structure, wherein the anatomical shell is based on a plurality of signals sensed by a mapping probe and wherein each of the plurality of signals includes a respective sensed voltage; receiving, from the user input device, a user input specifying a first target depth for editing; receiving, from a user input device, a selection of a first region of the anatomical shell; generating a first modified anatomical shell by: removing a first portion of the anatomical shell, the first portion of the anatomical shell comprising the selected first region of the surface and extending inward to a first editing depth based on the first target depth, the first editing depth comprising at least one finite depth, and generating a first new surface region on the second modified anatomical shell, corresponding to the selected region, wherein the first new surface is disposed at the first editing depth and includes at least one representation of a sensed voltage at the first editing depth; outputting, to the display device, the modified anatomical shell; receiving, from the user input device, a command to undo the generation of the modified anatomical shell; regenerating the anatomical shell; outputting the regenerated anatomical shell to the display device; receiving, from the user input device, a user input specifying a second target depth for editing; receiving, from a user input device, a selection of a second region of the anatomical shell, the second region comprising at least a portion of the first region; generating a second modified anatomical shell by: removing a second portion of the anatomical shell, the second portion of the anatomical shell comprising the selected second region of the surface and extending inward to a second editing depth based on the second target depth, the second editing depth comprising at least one finite depth, and generating a second new surface region on the second modified anatomical shell, corresponding to the selected second region, wherein the second new surface is disposed at the second editing depth and includes at least one representation of a sensed voltage at the second editing depth; and outputting, to the display device, the second modified anatomical shell.

In an Example 17, the method of Example 16, wherein the at least one representation of a sensed voltage at the first editing depth indicates a voltage magnitude corresponding to a blood pool.

In an Example 18, the method of Example 16, wherein the at least one representation of a sensed voltage at the second editing depth indicates a voltage magnitude corresponding to cardiac tissue.

In an Example 19, the method of Example 16, wherein the first target depth is at least 1 millimeter and at most 5 millimeters.

In an Example 20, the method of Example 19, wherein the second target depth is less than the first target depth.

In an Example 21, a system, comprising: a mapping probe configured to sense a plurality of signals associated with a cardiac structure; a processing device configured to: generate a first anatomical shell, wherein the first anatomical shell comprises a first surface that intersects a first plurality of mesh points, the first plurality of mesh points corresponding to a plurality of signals, wherein each of the plurality of signals includes at least one respective sensed electrical signal; select a test point, wherein the first surface does not intersect the test point, the test point having a position within a test neighborhood of a position of a first mesh point; determine a first value of a metric corresponding to the first mesh point; determine a second value of the metric corresponding to the test point; compute a gradient feature of the metric based on the first and second values; determine whether the gradient feature satisfies a condition; and generate a second anatomical shell, wherein the second anatomical shell comprises a second surface that intersects a second plurality of mesh points; wherein if the gradient feature satisfies the condition, the second plurality of mesh points includes the test point, and if the gradient feature does not satisfy the condition, the second plurality of mesh points does not include the test point; and a display device configured to display the second anatomical shell.

In an Example 22, the system of Example 21, wherein the metric comprises at least one of an out-of-cardiac-band impedance measurement, a unipolar electrode activation voltage measurement, a contact force measurement of the mapping probe, and a position-based cardiac motion measurement.

In an Example 23, a processor-based method for anatomical shell editing, the method comprising: generating a first anatomical shell, wherein the first anatomical shell comprises a first surface that intersects a first plurality of mesh points, the first plurality of points corresponding to a plurality of signals, wherein each of the plurality of signals includes at least one respective sensed electrical signal; selecting a test point, wherein the first surface does not intersect the test point, the test point having a position within a test neighborhood of a position of a first mesh point; performing a test associated with the test point, comprising: determining a first value of a metric corresponding to the first mesh point; determining a second value of the metric corresponding to the test point; computing a gradient feature of the metric based on the first and second values; determining whether the gradient feature satisfies a condition; and generating a second anatomical shell, wherein the second anatomical shell comprises a second surface that intersects a second plurality of mesh points, wherein: if the gradient feature satisfies the condition, the second plurality of mesh points includes the test point; and if the gradient feature does not satisfy the condition, the second plurality of mesh points does not include the test point.

In an Example 24, the method of Example 23, wherein, if the gradient feature does not satisfy the condition, the method further comprising: selecting an additional test point, the additional test point having a position within the test neighborhood of the position of the first mesh points; and performing the test associated with the additional test point.

In an Example 25, the method of Example 23, wherein the position of the test point is located opposite the direction of a normal to the first surface at the first mesh point.

In an Example 26, the method of Example 23, wherein the test neighborhood is a sphere with a radius of 2 millimeters.

In an Example 27, the method of Example 23, wherein the metric comprises at least one of an out-of-cardiac-band impedance measurement, a unipolar electrode activation voltage measurement, a contact force measurement of the mapping probe, and a position-based cardiac motion measurement.

In an Example 28, the method of Example 23, wherein performing the test further comprises: determining a sensed voltage value corresponding to the test point; and determining whether the sensed voltage value exceeds a voltage threshold.

In an Example 29, The method according to Example 28, wherein: if the gradient feature satisfies the condition and the sensed voltage value exceeds the voltage threshold, the second plurality of mesh points includes the test point; and if the gradient feature does not satisfy the condition or the sensed voltage value does not exceed the voltage threshold, the second plurality of mesh points does not include the test point.

In an Example 30, the method of Example 23, wherein determining whether the gradient feature satisfies a condition comprises determining whether an absolute value of the gradient feature exceeds a gradient threshold.

In an Example 31, a computer program product comprising a non-transitory computer readable storage medium containing program code, the computer program code when executed by a processor causes the processor to: generate a first anatomical shell, wherein the first anatomical shell comprises a first surface that intersects a first plurality of mesh points, the first plurality of points corresponding to a plurality of signals, wherein each of the plurality of signals includes at least one respective sensed electrical signal; select a test point, wherein the first surface does not intersect the test point, the test point having a position within a test neighborhood of a position of a first mesh point; perform a test associated with the test point, comprising: determining a first value of a metric corresponding to the first mesh point; determining a second value of the metric corresponding to the test point; computing a gradient feature of the metric based on the first and second values; determining whether the gradient feature satisfies a condition; and generate a second anatomical shell, wherein the second anatomical shell comprises a second surface that intersects a second plurality of mesh points, wherein: if the gradient feature satisfies the condition, the second plurality of mesh points includes the test point; and if the gradient feature does not satisfy the condition, the second plurality of mesh points does not include the test point.

In an Example 32, the computer program product of Example 31, wherein, if the gradient feature does not satisfy the condition, the computer program code when executed by a processor causes the processor to: select an additional test point, the additional test point having a position within the test neighborhood of the position of the first mesh points; and perform the test associated with the additional test point.

In an Example 33, the computer program product of Example 31, wherein the position of the test point is located opposite the direction of a normal to the first surface at the first mesh point.

In an Example 34, the computer program product of Example 31, wherein the metric comprises at least one of an out-of-cardiac-band impedance measurement, a unipolar electrode activation voltage measurement, a contact force measurement of the mapping probe, and a position-based cardiac motion measurement.

In an Example 35, the computer program product of Example 31, wherein performing the test further comprises: determining a sensed voltage value corresponding to the test point; and determining whether the sensed voltage value exceeds a voltage threshold, wherein if the gradient feature satisfies the condition and the sensed voltage value exceeds the voltage threshold, the second plurality of mesh points includes the test point; and if the gradient feature does not satisfy the condition or the sensed voltage value does not exceed the voltage threshold, the second plurality of mesh points does not include the test point.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
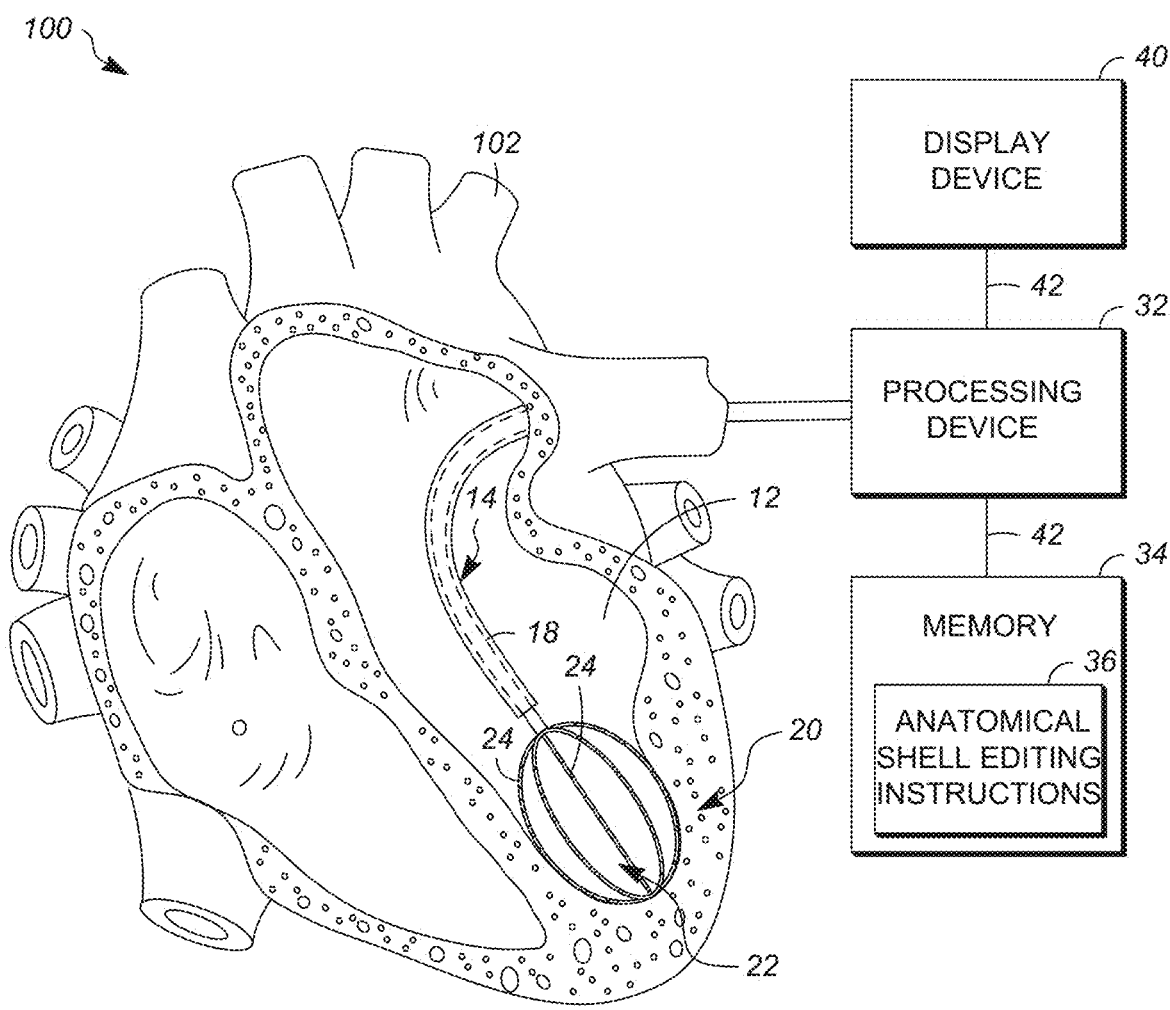
FIG. 1 is a schematic view of a system for mapping and viewing internal cardiac structures, in accordance with embodiments of the present disclosure.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

FIG. 1 is a schematic view of a mapping system 100 for mapping cardiac structures 102, in accordance with embodiments of the disclosure. Throughout this disclosure, the term "cardiac structure" can mean any portion of a subject's heart and/or adjacent features such as, for example, an endocardium, an epicardium, an entire heart, a heart chamber, a portion of a heart chamber, a valve, a coronary sinus and/or its tributaries, a portion of a coronary sinus and/or a portion of its tributaries, a pulmonary artery, other surrounding vasculature and/or the like. While this disclosure discusses using the mapping system 100 to map cardiac structures 102, embodiments of the mapping system 100 may also, or alternatively, be used to map other organs and biological tissue including, but not limited to, kidneys, lungs, brains, gall bladders, livers, spleens, intestines and/or the like.

The system 100 includes a mapping probe 14. The mapping probe 14 includes a flexible catheter body 18. When mapping cardiac structures 102, a physician or medical professional inserts the distal end of the catheter body 18 into a cardiac chamber (e.g., the left ventricle of the heart) of a patient. While the left ventricle of the heart is shown, alternatively, the distal end of the catheter body 18 can be deployed in other parts of the heart and/or surrounding vasculature, such as, e.g., the left atrium, the right atrium, or the right ventricle, the coronary sinus and its tributaries and the pulmonary artery. The distal end of the catheter body 18 has a multiple electrode structure 20. In the illustrated embodiments, the electrode structure 20 takes the form of a basket defining an open interior space 22. While the electrode structure 20 takes the form of a basket in the illustrated embodiments, this is only an example and other electrode structures can be utilized. For example, the electrode structure may include one or more electrodes (e.g., ablation electrodes, microelectrodes, ring electrodes, etc.) disposed on an ablation catheter, a diagnostic catheter, and/or the like.

As shown in FIG. 1, the electrode structure 20 includes a number of electrodes 24. The electrodes 24 are configured to sense electrical signals traversing the cardiac structure 102. The electrical signals can be sensed on the endocardium surface of the heart and/or in the heart chamber below the endocardium surface. As used herein, a mapped representation of a signal that is sensed at a point inside a heart chamber is referred to as being below the endocardium surface. That is, for example, because the map includes an anatomical shell that represents an endocardium surface and, from the perspective of the viewer, a point that is located inside the chamber, and not on the endocardium surface, would appear to be below the mapped surface.

Each signal may be associated with a set of respective position coordinates that correspond to the location at which the signal was sensed. The respective electrical signals can include, but are not limited to, voltage magnitudes, activation signals and changes in activation signals over a period of time. Each of the respective position coordinates may include three-dimensional Cartesian coordinates, polar coordinates, and/or the like. In embodiments, other coordinate systems can be used. In embodiments, an arbitrary origin is used and the respective position coordinates refer to positions in space relative to the arbitrary origin. Since, in embodiments, the signals may be sensed on the endocardium surface as well as in the chamber enclosed by the endocardium surface, the respective position coordinates may be on the endocardium surface of the patient's heart and/or below the endocardium surface.

The electrodes 24 are electrically coupled to a processing device 32. That is, each electrode 24 on the basket structure 20 may be communicatively coupled to the processing device 32, via a wired and/or wireless connection. In embodiments where there is a wired connection, the wires (not shown) from each electrode may extend through the catheter body 18 of the mapping probe 14 and electrically couple each electrode 24 to the processing device 32. In embodiments where there is a wireless connection, a transmitter (not shown) may be included in the mapping probe 14 which may transmit sensed signals from each electrode 24 on the basket structure 20 to a receiver (not shown) that is coupled to the processing device 32.

Once the sensed points are received by the processing device 32 from the electrodes 24, the processing device 32 processes the sensed signals. The processing device 32 processes the sensed points according to anatomical shell editing instructions 36, which are stored on memory 34. The processing device 32 may be, include, or be included in, an electrical processor, a software processor, a general purpose microprocessor and/or a special purpose microprocessor, and may include a sole processor or one of multiple processors or cores. The processed signals are displayed on a display device 40. The display device 40 can include, but is not limited to, one of the following display devices: a cathode ray tube (CRT) display, a light emitting diode (LED) display, or a liquid crystal display (LCD) display.

The memory 34 can be in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a processing device 32 such as, for example, quantum state memory, and/or the like. Mapping instructions 36 may be programmed on the memory 34 using any number of different programming environments, including various languages, development kits, frameworks, and/or the like. Some or all of the functionality contemplated herein may also, or alternatively, be implemented in hardware and/or firmware.

The processing device 32, the memory 34 and the display device 40 can be coupled together, directly and/or indirectly, by a bus 42. Any number of additional components, different components, and/or combinations of components may also be coupled to the processing device 32, memory 34 and display device 40, via the bus 42. The bus represents what may be one or more busses (such as, for example, an address bus, data bus, or combination thereof).

The illustrative mapping system 100 shown in FIG. 1 is not intended to suggest any limitation as to the scope of use or functionality of embodiments of the present disclosure. Neither should the illustrative mapping system 100 be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure. For example, the memory 34 may be integrated with the processing device 32.

Figure 2:
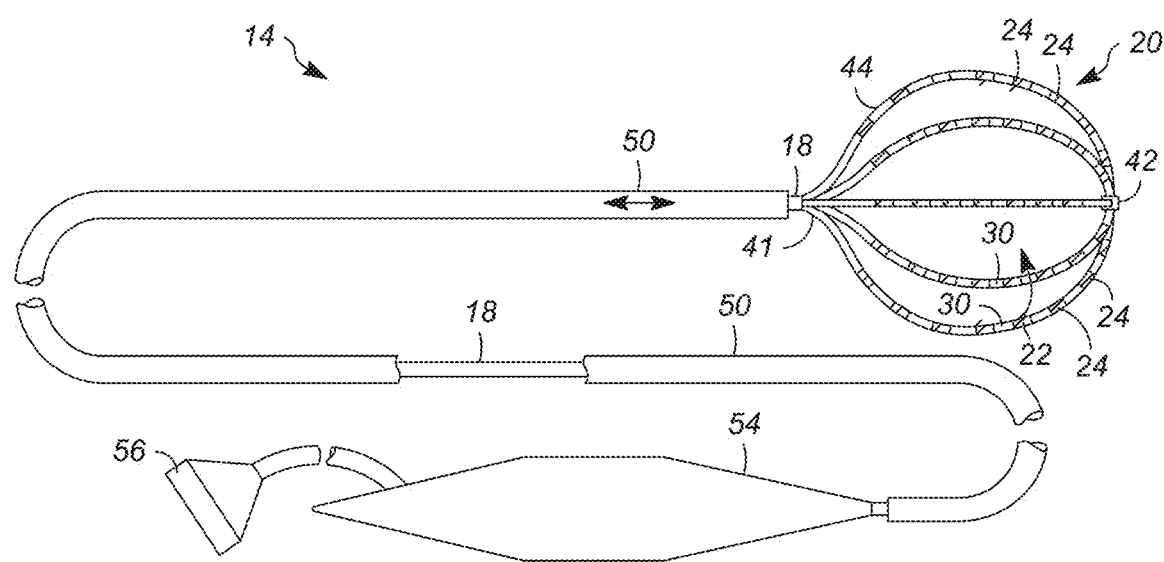
FIG. 2 is a schematic view of a mapping probe for use in association with the system of FIG. 1, in accordance with embodiments of the disclosure.

FIG. 2 is a schematic view of a mapping probe 14 for use in association with the system 100 of FIG. 1, in accordance with embodiments of the disclosure. The mapping probe 14 has a flexible catheter body 18, the distal end of which carries the three-dimensional basket structure 20 that includes the mapping electrodes 24. As stated above, the mapping electrodes 24 sense signals in a cardiac structure; and the sensed signals are sent to a processing device 32, via a wired and/or wireless connection. The processing device 32 processes the sensed signals and a map is created, as described, for example, in the description corresponding to FIG. 3, below. The types of maps created can include, but are not limited to, the following: a voltage map, an activation map, a fractionation map, a velocity map, and/or the like.

The basket structure 20 comprises a base member 41 and an end cap 42 between which flexible splines 44 generally extend in a circumferentially spaced relationship. As discussed above, the basket structure 20 takes the form of a basket defining an open interior space 22. In embodiments, the splines 44 are made of a resilient inert material, such as Nitinol metal or silicone rubber, and are connected between the base member 41 and the end cap 42 in a resilient, pre-tensed condition, to bend and conform to the tissue surface they contact. In the illustrated embodiments, eight splines 44 form the three-dimensional structure 20. Additional or fewer splines 44 could be used in other embodiments, and the three-dimensional structure 20 may be configured according to any number of different shapes such as, for example, generally spherical shapes, generally elliptical shapes, generally tear-drop shapes, and/or the like. As illustrated, each spline 44 carries eight mapping electrodes 24. Additional or fewer mapping electrodes 24 could be disposed on each spline 44 in other embodiments of the three-dimensional structure 20. In the illustrated embodiments, the three-dimensional structure 20 is relatively small (e.g., 40 mm or less in diameter). In embodiments, the three-dimensional structure 20 is larger (e.g., 40 mm in diameter or greater).

In embodiments, a slidable sheath 50 is movable along the major axis of the catheter body 30. Moving the sheath 50 forward (i.e., toward the distal end) causes the sheath 50 to move over the three-dimensional structure 20, thereby collapsing the structure 20 into a compact, low profile condition suitable for introduction into an interior space, such as, for example, into the heart. In contrast, moving the sheath 50 rearward (i.e., toward the proximal end) exposes the three-dimensional structure 20, allowing the structure 20 to elastically expand and assume the pre-tensed position illustrated in FIG. 2. Further details of embodiments of the three-dimensional structure 20 are disclosed, for example, in U.S. Pat. No. 5,647,870, entitled "Multiple Electrode Support Structures," which is hereby incorporated by reference in its entirety.

In embodiments where the mapping probe 14 uses a wired connection, a signal wire (not shown) may be electrically coupled to each mapping electrode 24. The wires may extend through the body 30 of the mapping catheter 20 into a handle 54, in which they may be coupled to an external connector 56, which may be, for example, a multiple pin connector. The connector 56 electrically couples the mapping electrodes 24 to the processing system 32. Further details on mapping systems and methods for processing signal generated by mapping catheters are discussed, for example, in U.S. Pat. No. 6,070,094, entitled "Systems and Methods for Guiding Movable Electrode Elements within Multiple-Electrode Structure;" U.S. Pat. No. 6,233,491, entitled "Cardiac Mapping and Ablation Systems;" and U.S. Pat. No. 6,735,465, entitled "Systems and Processes for Refining a Registered Map of a Body Cavity," the disclosures of which are incorporated herein by reference.

It is noted that other electrode structures could be deployed on the distal end of a mapping catheter. It is further noted that the multiple mapping electrodes 24 may be disposed on more than one structure, rather than, for example, the single mapping probe 14 illustrated in FIG. 2. For example, if mapping within the left atrium with multiple mapping structures, an arrangement comprising a coronary sinus catheter carrying multiple mapping electrodes and a basket catheter carrying multiple mapping electrodes positioned in the left atrium may be used. As another example, if mapping within the right atrium with multiple mapping structures, an arrangement comprising a decapolar catheter carrying multiple mapping electrodes for positioning in the coronary sinus, and a loop catheter carrying multiple mapping electrodes for positioning around the tricuspid annulus may be used.

Although the mapping electrodes 24 have been described as being carried by dedicated mapping probes, such as the mapping probe 14, the mapping electrodes may be carried on non-mapping dedicated probes or multifunction probes. For example, an ablation catheter can be configured to include one or more mapping electrodes 24 disposed on the distal end of the catheter body and coupled to the signal processing system 32.

Figure 3:
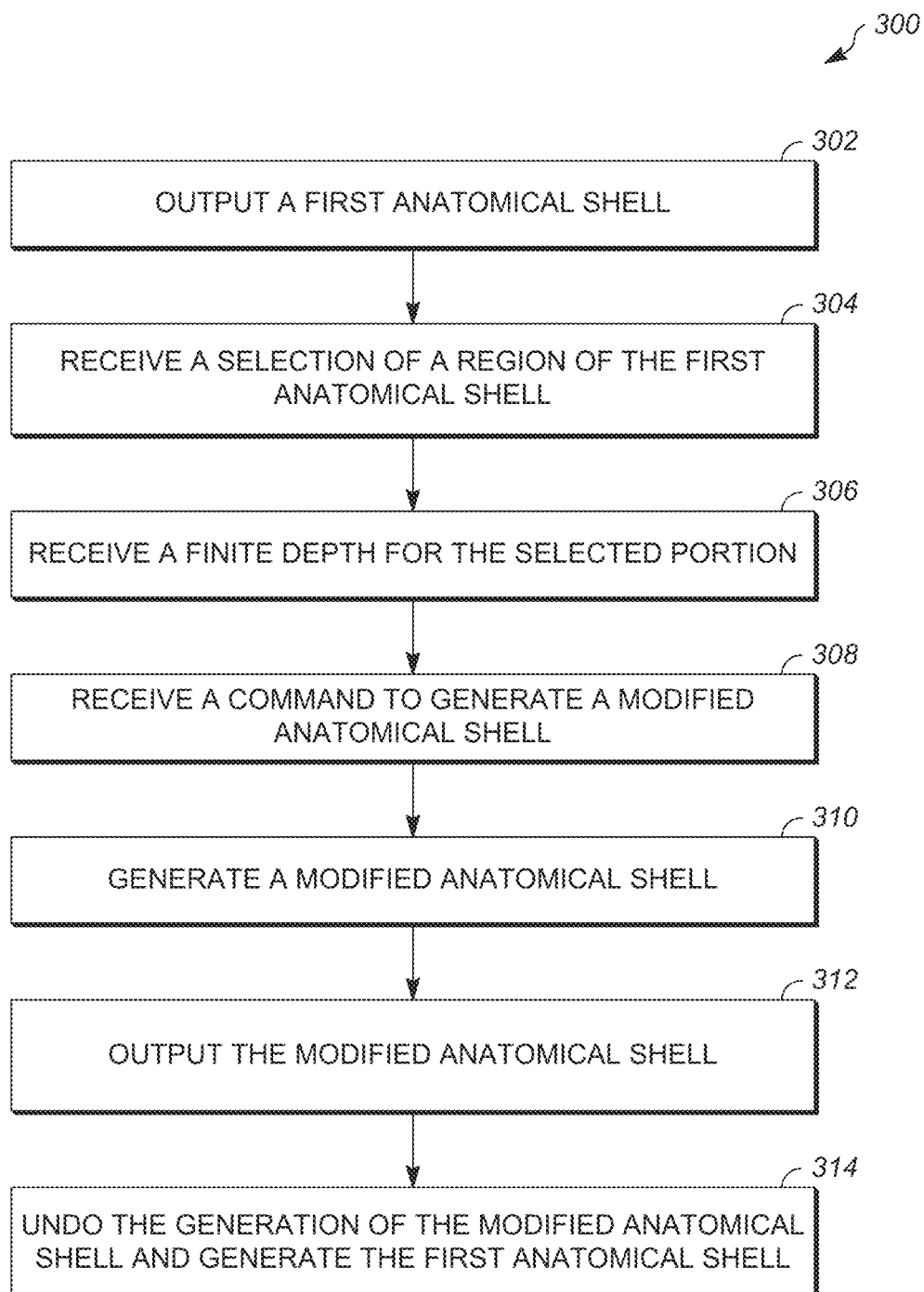
FIG. 3 is a flow diagram depicting an illustrative processor-implemented method for anatomical shell editing, in accordance with embodiments of the disclosure.

FIG. 3 is a flow diagram of a processor-based method 300 for adjustable depth anatomical shell editing, in accordance with embodiments of the disclosure. Embodiments of method 300 may be performed, in whole or in part, by a mapping system (e.g., the mapping system 100 depicted in FIG. 1). Method 300 includes outputting a first anatomical shell of a cardiac structure to a display device (block 302). The first anatomical shell includes representations of a plurality of voltages associated with the cardiac structure at a plurality of points, wherein the plurality of voltages are sensed by a mapping probe. In embodiments, the mapping probe can have the same or similar characteristics to the mapping probe 14 described above in FIGS. 1 and 2. In embodiments, the cardiac structure can include, but is not limited to, a portion of the left atrium, a portion of the right atrium, a portion of the left ventricle, a portion of the right ventricle, a portion of the coronary sinus and/or a portion of its tributaries, a portion of other surrounding vasculature or the complete chamber of the left atrium, the right atrium, the left ventricle, the right ventricle, the coronary sinus and its tributaries or the surrounding vasculature.

Each of the plurality of voltages sensed by the mapping probe has a corresponding set of three-dimensional position coordinates. The three-dimensional position coordinates for a sensed voltage is referred to as the point at which the voltage was sensed. In embodiments, the points may be represented in Cartesian coordinates. However, other coordinate systems can be used. In embodiments, an arbitrary origin is used and the points are defined with respect to the arbitrary origin. In some embodiments, the points have non-uniform spacing, while in other embodiments, the points have uniform spacing. In embodiments, a point corresponding to a sensed voltage may be located on the endocardium surface of the heart and/or below to the endocardium surface of the heart.

In embodiments, the anatomical shell may be generated based, at least in part, on the electrical signals. The shell may be generated, at least in part, using any number of other signals, techniques, and/or the like. For example, embodiments may utilize impedance mapping techniques to generate the shell. In embodiments, a surface may be fitted on one or more of the points associated with the electrical signals to generate a shell representing the endocardium surface. In embodiments, one or more features of the electrical signals at the corresponding points can be included in the map of the endocardium surface. For example, embodiments may include displaying annotations on the shell that represent features extracted from the electrical signals such as, for example, voltages, activation amplitudes, signal sharpness and/or the like. As another example, a surface may be fitted on one or more of the points associated with the electrical signals to generate a shell representing an epicardium surface or other excitable cardiac tissue.

Figure 4A:
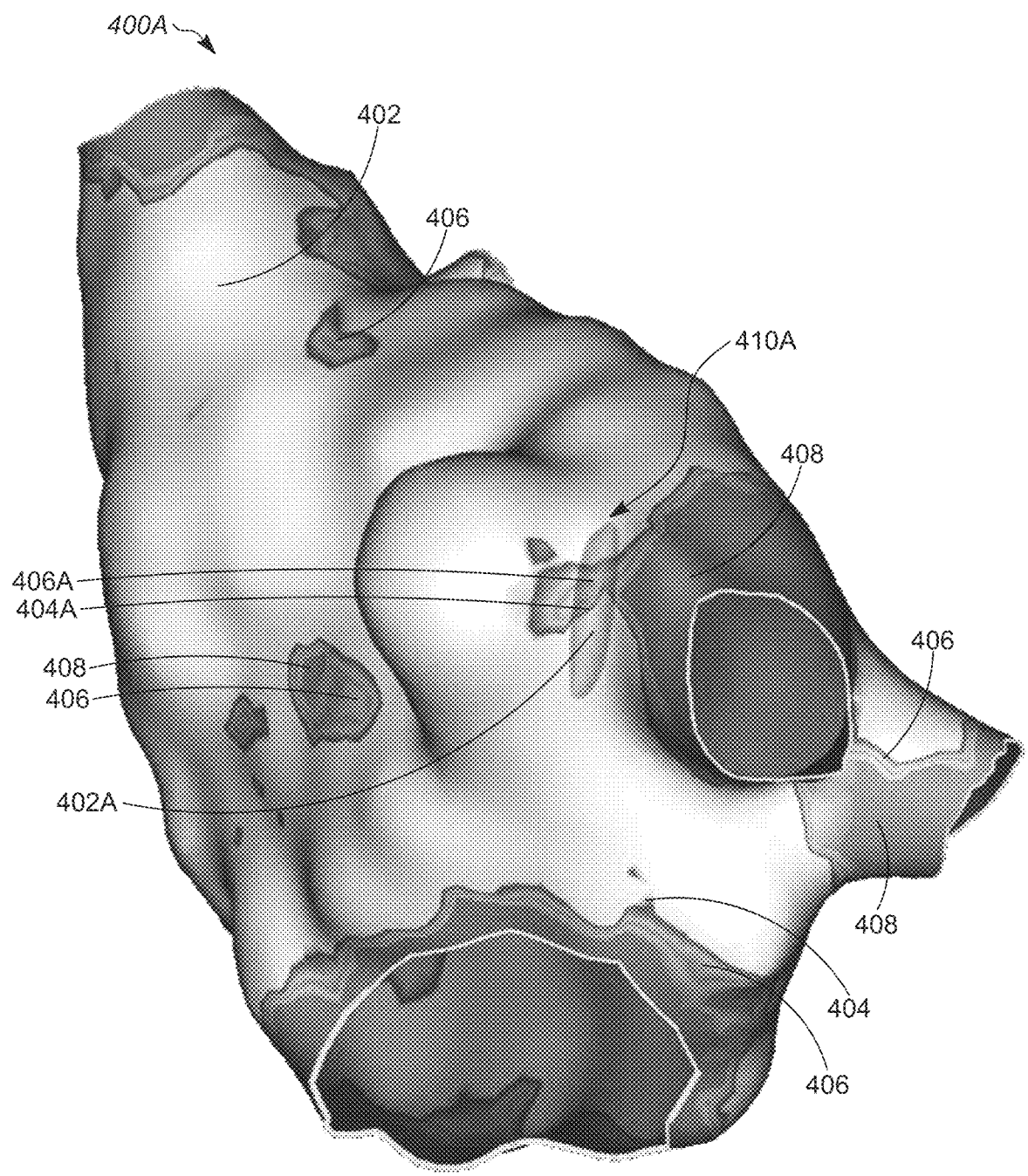
FIGS. 4A-4D are images of an anatomical shell shown from different perspectives, in accordance with embodiments of the disclosure.

An image of an illustrative first anatomical shell 400A outputted to a display device is shown in FIG. 4A. The different shades of grey correspond to different voltages sensed by the mapping probe. More specifically, the first portion 402, the second portion 404, the third portion 406 and the fourth portion 408 each have different, respective, voltage magnitudes (or range of voltage magnitudes). The first portion 402 has a higher voltage magnitude than the second portion 404, the second portion 404 has a higher voltage magnitude than the third portion 406 and the third portion 406 has a higher voltage than the fourth portion 408.

Embodiments of method 300 also include receiving, from a user input device, a selection of a region of the first anatomical shell (block 304). The user input device used to make the selection may include a mouse, a touchscreen and/or the like, that is used to manipulate a selection tool that is provided on a user interface provided by the display device. The selection tool may include, for example, a brush, a cursor for enclosing the selected region by drawing a freeform shape around the region, an expandable polygon selection tool, and/or the like, and may be, in embodiments, selected from a number of optional selection tools. In embodiments, the selection tool may have an adjustable size, behavior and/or other characteristics thereof. In this manner, for example, a user may select a desired selection tool and a size thereof. Selecting a region of the surface of the anatomical shell may include, for example, circling the region of the surface of the anatomical shell using a mouse or touchscreen device to manipulate a cursor, brushing over the region of the surface using an input device to manipulate a brush, and/or the like.

Referring to FIG. 4A, for example, a selected region 410A is shown. The selected region 410A includes three regions, a first region 402A, a second region 404A, and a third region 406A, each having representations of different voltages. The different voltages may be represented, for example, using different colors, shading, textures, and/or the like. The first region 402A has the same voltage as the region 402, which is higher than the voltage of the second region 404A, which has the same voltage as the regions 404. And, the second region 404A has a higher voltage than the third region 406A, which has the same voltage as the regions 406. From the different voltage magnitudes sensed in the three regions 402A, 404A, 406A, a user may determine that the system did not accurately represent all of the voltage magnitudes in the selected region 410A. In particular, for example, the user may determine that the second region 404A and the third region 406A should have a voltage magnitude closer to the first region 402A. Alternatively, or additionally, a user familiar with the cardiac anatomy may recognize that the anatomical shell 400A is not accurately represented because, for example, the user knows that the cardiac chamber has an internal protrusion near the second region 404A and the third region 406A that is not shown on the shell 400A. By employing embodiments provided herein, however, the anatomical shell 400A may be edited to more accurately represent the cardiac structure, as explained below.

In some embodiments, method 300 may also include receiving, from an input device, a modification to the selection of the region of the surface of the anatomical shell. In response to receiving the modification, the modified selection may be made of a region of the surface of the anatomical shell. Being able to modify the selection may be useful to a user that selected too big or too small of a region, for facilitating incremental selection, to facilitate more accurate selection, and/or the like. In embodiments, a modification to the selection may include a modification to the target depth of the selection, a modification to the size of the region of the surface selected, and/or the like. For example, in embodiments, the modification may include a selection of an additional region of the surface of the anatomical shell. Similar to selecting a portion above, a mouse, touchscreen or the like can be used to modify the selection. In embodiments, modifying the selected portion may include deselecting the selected region and then reselecting a region. In embodiments, modifying the selection may include modifying the selection by altering the boundaries of the selection. In embodiments this may be done, for example, by clicking on a portion of the border of the selected region and dragging the selected portion of the border to a new location.

Embodiments of method 300 also include receiving, from a user input device, a target depth for the selected region (block 306). Using the received target depth, the selected region 410A may be removed to an editing depth that is based on the target depth and that follows the contour of the anatomical shell 400A. In embodiments, the removed portion includes the selected region (or modified selected region) of the surface and extending inward to an editing depth. The editing depth may include at least one finite depth and may vary, corresponding to the contour of the surface of the anatomical shell. That is, for example, the editing depth may be the distance, along an axis normal to the surface of the anatomical shell, between a point on the surface of the anatomical shell and a point inward from the surface (i.e., below the surface) of the anatomical shell. In that manner, the editing depth may change with the contour of the surface.

According to embodiments, the editing depth may be adjustable and/or selectable. That is, for example, a user may input and/or select a target depth, via the user interface, such that the editing depth, corresponding to each point in the selected region, may be at least approximately equal to the target depth (e.g., equal to the target depth, within at least 0.1 millimeters of the target depth, within at least 0.5 millimeters of the target depth, within 1 millimeter of the target depth, and/or the like. In embodiments, the target depth may be less than one millimeter, at least one millimeter and no more than 10 millimeters, at least one millimeter and no more than 5 millimeters, and/or the like.

In embodiments, method 300 can include receiving, from a user input device, a command to rotate the displayed anatomical shell 400A after the region 410A is selected, before the region 410A is selected, and/or at any time while the anatomical shell 400A is displayed. The method 300 can include generating a rotated view of the first anatomical shell based on the command. In embodiments, the anatomical shell 400A may be rotated in any direction. Additionally, any number of other methods of adjusting a displayed image may be employed such as, for example, zoom, pan, invert, and/or the like. Additionally, any number of different colors, textures, and/or the like may be implemented, adjusted, and/or selected for representing various displayed features such as, for example, anatomical features, voltage magnitudes, signal sharpness, activation amplitudes, activation propagations, and/or the like.

In embodiments, method 300 can include receiving, from a user input device, a command to generate the modified anatomical shape (block 308). Therefore, instead of automatically generating the modified shape once the region 410A is selected, the processor-based method waits until a user inputs a command to generate the modified anatomical shape. This can be useful to determine whether the selected region 410A is what the user intended to select. Embodiments of the disclosure also include automatically generating the modified anatomical shape, based on the selected region.

Embodiments of method 300 also include generating a modified (second) anatomical shell that includes the at least one voltage sensed by the mapping probe at approximately the finite depth for the selected portion (block 310). That is, in embodiments, the modified anatomical shell has the same shape and voltages as the first anatomical shell 400A, except that the selected portion 410A displays the voltage(s) sensed by the mapping probe at approximately the finite depth. In embodiments, the modified anatomical shell may be altered in shape to indicate the presence or absence of a feature, structure, and/or the like. In embodiments, the selected region may be removed to the editing depth, in the modified anatomical shell, with a new surface region being generated at the editing depth, upon which is displayed the respective voltage values. After the modified anatomical shape is generated, embodiments of method 300 include outputting the modified anatomical shell to the display device (block 312). The display device may have some or all of the same characteristics as the display device 40 in FIG. 1.

Figure 4B:
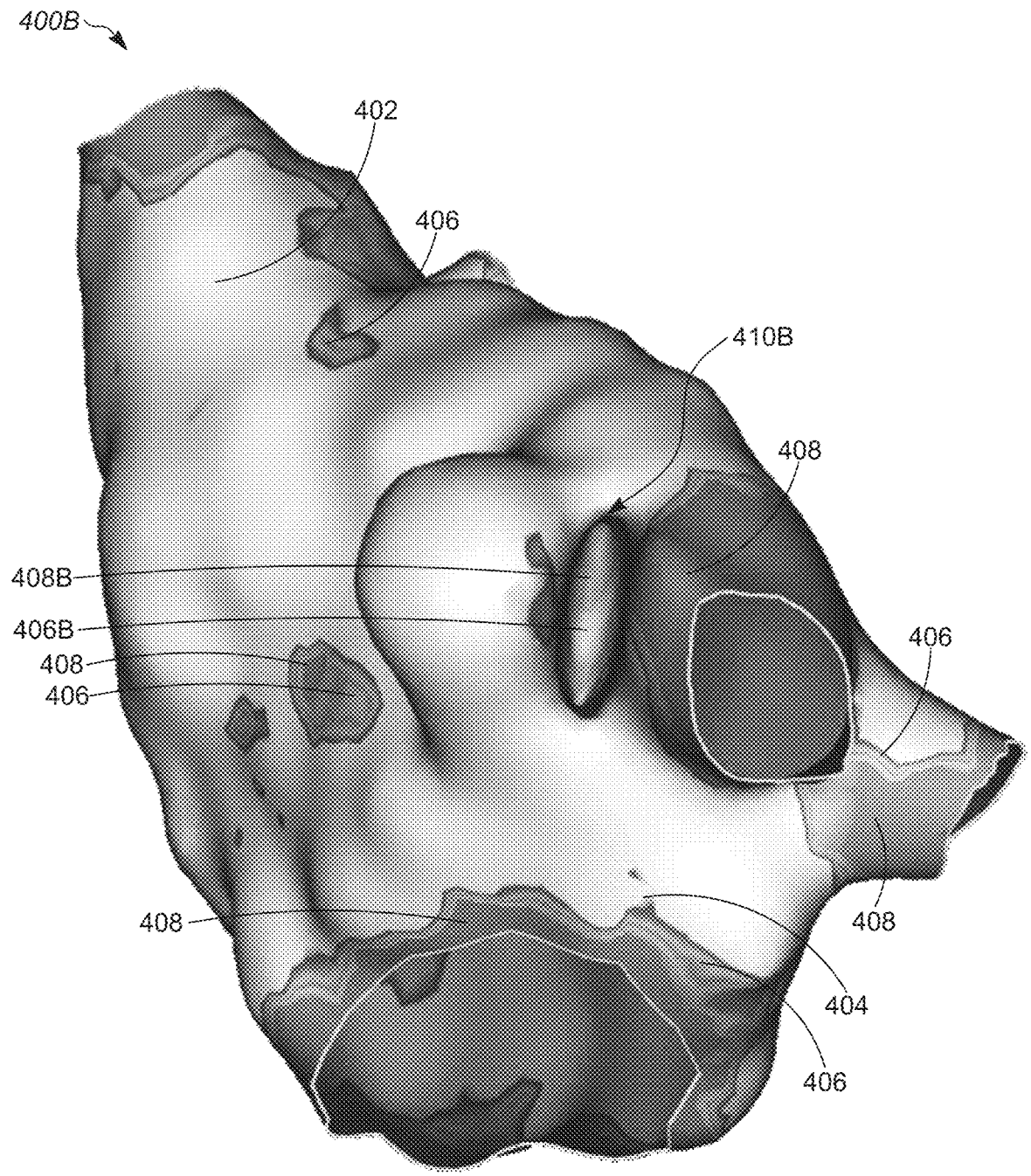

An image of an exemplary modified anatomical shell 400B outputted to a display device is shown in FIG. 4B. As shown, the selected region 410B of the modified anatomical shell 400B has different voltage magnitudes than the selected region 410A of the first anatomical shell 400A. In particular, the selected region 410B now includes a region 408B that has the same voltage magnitude as the fourth regions 408 and a region 406B that has the same voltage magnitude as the third regions 406. In embodiments, a user and/or a processing device (e.g., the processing device 32 depicted in FIG. 1) may determine that since the regions 406B, 408B have such low voltage magnitudes, the regions 406B, 508B likely correspond to blood pools. In this manner, since the regions 406B, 408B have voltage magnitudes that roughly correspond to voltage magnitudes sense in blood pools, a user may, for example, determine that the selected target depth was likely too deep. As a result, in embodiments, method 300 can include receiving a command from a user input device to undo the generation of the modified anatomical shell and regenerate the first anatomical shell (block 314). When the first anatomical shell is generated, it can be output to the display device for the user to view.

Figure 4C:
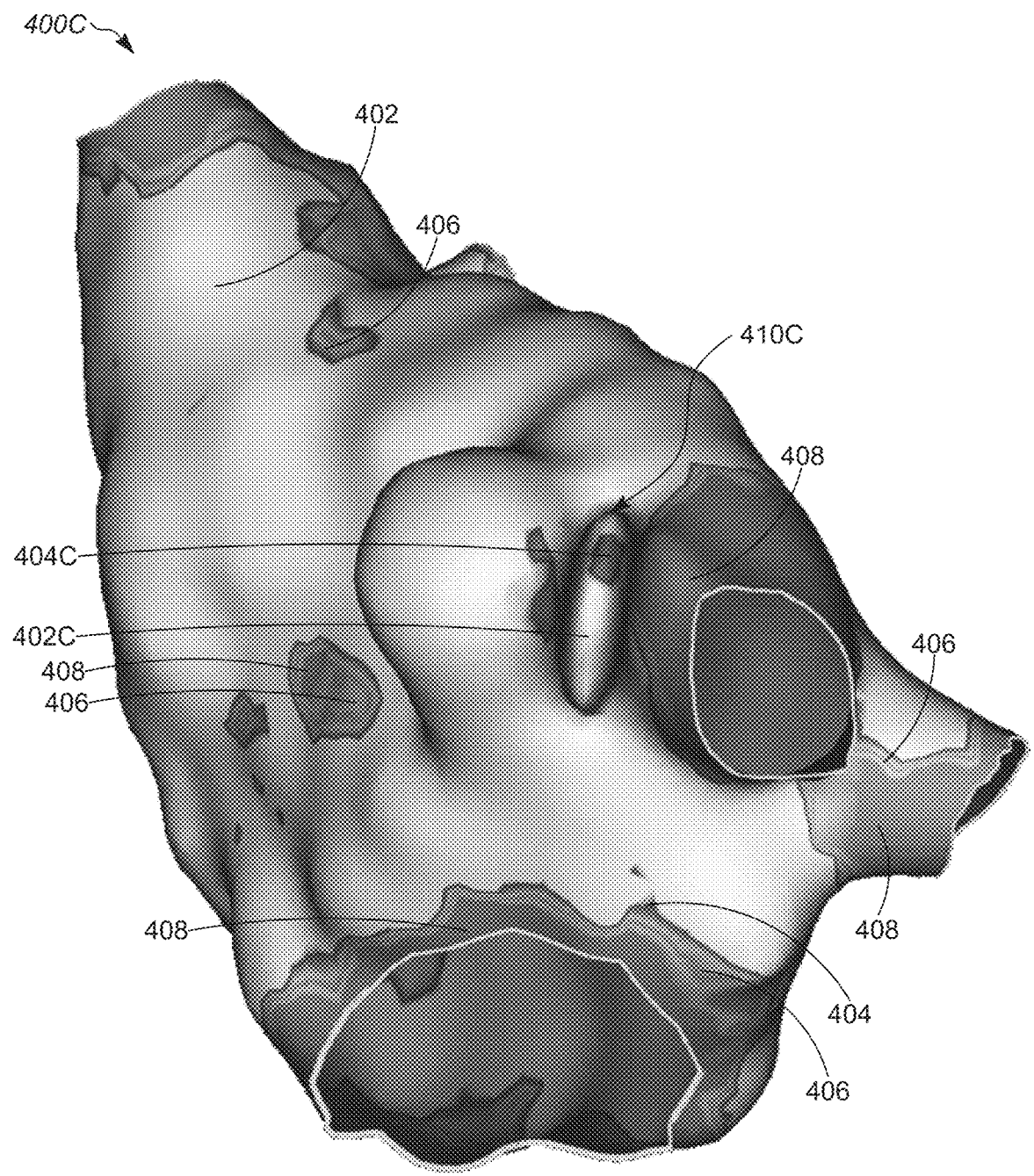

After a user chooses to undo the generation of the modified anatomical shell 400B, a user may then modify the selected region 410A, either by increasing or decreasing the boundary of the selected region 410A or changing the depth of the selected region 410A. In the example illustrated in FIGS. 4A-4D, the target depth was modified. Another (third) modified anatomical shell 400C may be created, using the modified selection (e.g., the modified target depth), as shown in FIG. 4C. As can be seen, higher voltage magnitudes are included in the selected region 410C. In particular, a region 402C has the same voltage magnitudes as the first regions 402 and a region 404C has the same voltage magnitudes as the second regions 404.

Figure 4D:
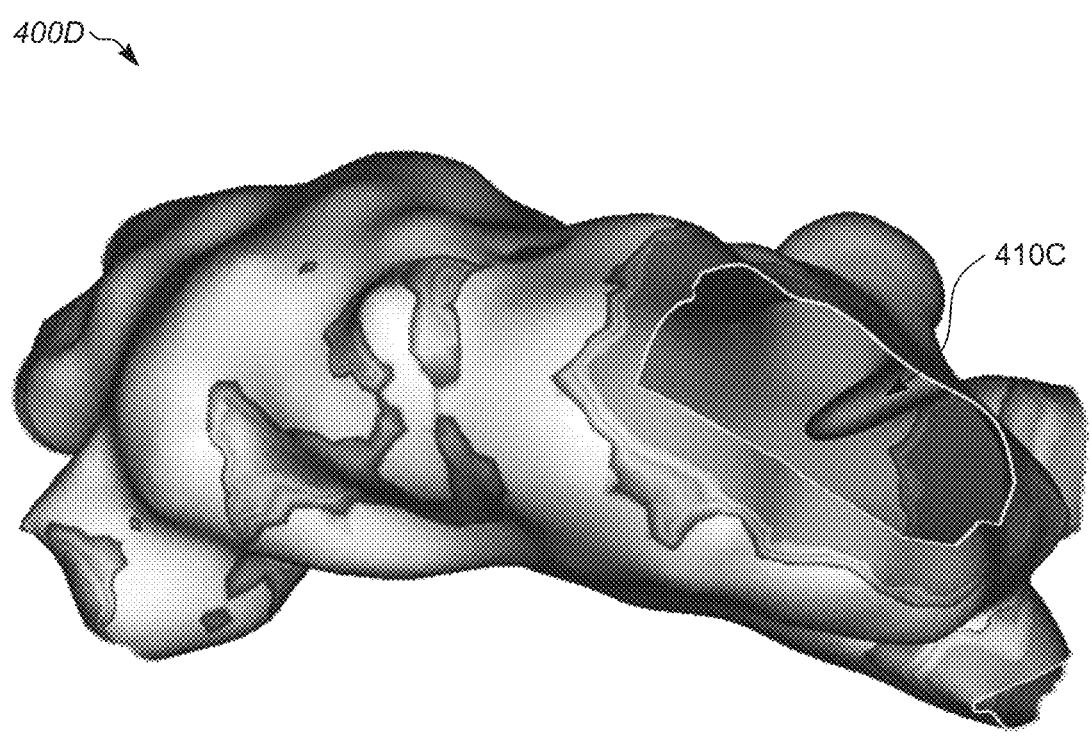

FIG. 4D is another, rotated, view of the modified anatomical shell 400C showing the selected region 410C. Due to this rotation, a user may tell that the modified target depth received resulted in a modified anatomical shell 400C that is likely closer in shape to the actual cardiac chamber than the first anatomical shell 400A and the modified anatomical shell 400B. If, on the other hand, several finite depths were attempted, which did not improve the voltage magnitude of the selected portion 410A in FIG. 4A, then a physician may be able to tell that the selected portion 410A is diseased and exhibiting less than ideal voltage activation. In this manner, a physician or other medical professional may better perform any necessary cardiac treatment on this cardiac chamber due to the increased accuracy of the displayed representation.

While embodiments of a user-directed method of voltage-guided anatomical shell editing are described above, embodiments of the disclosure include automated anatomical shell editing. In embodiments, for example, a processing device (e.g., the processing device 32 depicted in FIG. 1) may be configured to test points below the endocardium surface of a generated anatomical shell to determine whether anatomical features exist there, to determine voltage magnitudes at various points and depths, and/or the like. In embodiments, the processing device may be configured to utilize any number of different metrics such as, for example, voltage magnitudes, activation amplitudes, signal sharpness, out-of-cardiac-band impedance measurements, contact force measurements of the mapping probe, position-based cardiac motion measurements, and/or the like. Values of the metrics may be utilized in any number of various algorithms to identify internal structures and/or the like.

In embodiments, the chosen metric (or metrics) such as those listed above may tend to exhibit behaviors for which proximity to tissue will coincide with meaningful outliers, allowing for intelligent annotation and aggregation. The metric may also be some combination of those quantities. In embodiments, the metric may be a $R^3 \rightarrow R$ function, such that for every point where the metric was measured, a 3D position is recorded as well as a scalar value.

Figure 5:
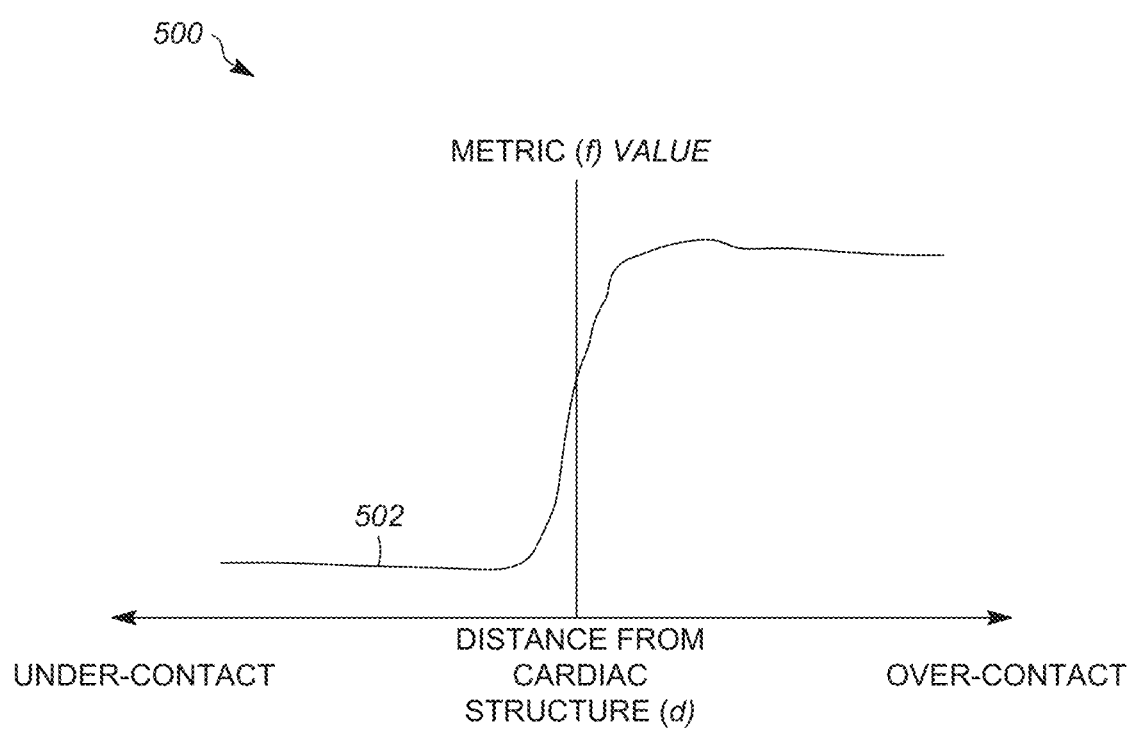
FIG. 5 is a graph of a metric, in accordance with embodiments of the disclosure.

In embodiments, a metric may be selected so that the likelihood, proximity, and/or degree of contact between an electrode (and/or mapping probe) and the cardiac structure at a particular point (e.g., a test point) can be determined. For example, by determining the likelihood, proximity, and/or degree of contact between an electrode (and/or mapping probe) and a cardiac structure, one may determine whether or not the generated anatomical shell is a distorted version of the actual shape of the cardiac structure. For example, an observation about the profile exhibited by embodiments of the metric is embodied in FIG. 5. FIG. 5 is a graph 500 of a metric 502 that may be used to model techniques for determining the likelihood, proximity, and/or degree of contact between an electrode (and/or mapping probe) and a cardiac structure is shown, in accordance with embodiments of the disclosure.

As illustrated in FIG. 5, the general mathematical model corresponding to the metric may be for example:

$$\text{For } |d| > \varepsilon, \left|\frac{df}{dx}\right| < \delta$$

where d is the distance of a location of a measured signal from a cardiac structure, e is a first threshold, and δ is a second threshold. Similarly, $$\text{For } |d| < \varepsilon, \left|\frac{df}{dx}\right| \gg \delta$$

That is, embodiments of the system may utilize the information that is in the gradient. For example, in the blood pool (e.g., in the case of under-contact), the values of the metric may be considered to be roughly uniform around some low mean, and conversely, for over-contact, the values may be considered to be roughly uniform around some high mean. The endocardium surface may be considered to be in the vicinity of the vertical axis (or, e.g., within ε of the vertical axis). This 1-dimensional model may be expanded to 3D, for example, by means of spatial quantization, if linearization by density is assumed. That is, for example, one may reduce the generalized 3D case, described by the similarly generalized 3D gradient, to a set of linear gradients taken between a set of selected points.

For example, a metric 502 may be chosen so that when there is a preferred amount (or likelihood) of contact between a mapping electrode and the cardiac structure, the gradient of the metric 502 is greater, and exceeds a threshold, than the gradient of the metric 502 when the mapping electrode is either not in contact with the cardiac structure or is distending the cardiac structure (e.g., in a situation of over-contact). In embodiments, a sensed electrical signal may exhibit the properties of metric 502 in FIG. 5 and may be selected to be the metric. In embodiments, the sensed electrical signal selected to be the metric may include, but is not limited to, one or more of the following: an out-of-cardiac-band impedance measurement, a unipolar electrode activation voltage measurement, a contact force measurement of the mapping probe, and a position-based cardiac motion measurement.

Figure 6A:
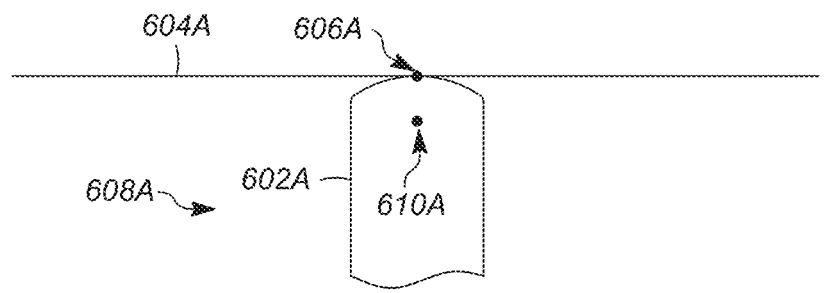
FIGS. 6A-6C illustrate different types of contact between an electrode and a cardiac structure, in accordance with embodiments of the disclosure.
Figure 6B:
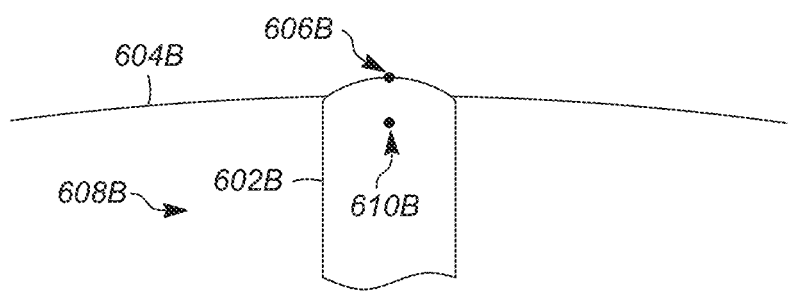
Figure 6C:
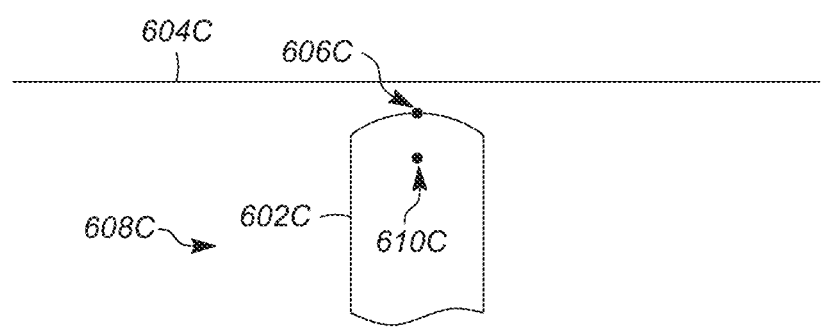

Referring to FIGS. 6A-6C, for example, three types of contact between an electrode 602A-602C and a cardiac structure 604A-604C are illustrated. In embodiments, the electrode 602A-602C may represent more than one electrode, a mapping probe, a catheter tip, and/or the like. For the purposes of clarity, the discussion will refer to an electrode, but this discussion is not meant to limit the scope of embodiments of the disclosure, and it is to be understood that a similar discussion may be applicable to multiple electrodes, a mapping probe, a catheter, and/or the like. For this example, assume an anatomical shape was generated that has a first surface that intersects the outermost points sensed by the mapping probe and that the metric is a sensed voltage.

Referring to FIG. 6A, the electrode 602A in this embodiment has a desirable amount of contact with the cardiac structure 604A at sensed point 606A. In particular, the electrode 602A is contacting the cardiac structure 604A at sensed point 606A, but is not pushing against the cardiac surface 604A and distorting it. Accordingly, a generated anatomical shell based on a signal sensed by a mapping electrode 602A having this type of contact with a cardiac structure 604A may closely resemble the actual shape of the cardiac structure 604A at the sensed point 606A. That is, for example, the sensed point 606A may be regarded as an appropriate point for displaying as a point on the surface, or mesh, of the anatomical shell.

According to embodiments, to determine whether the sensed point 606A is an appropriate surface point, a test, based on a gradient of one or more metrics, as discussed above, may be performed with respect to a test point 610A. In particular, a test point 610A may be selected that has a position within a test neighborhood of the position of the sensed point 606A. Since the sensed point 606A is one of the outermost points sensed by the mapping probe, the test point will be located below the cardiac structure surface 604A with respect to the sensed point 606A. Since the sensed point 606A is on the surface of the cardiac structure 804A, any point that is located below the surface 604A may be located in the blood pool 608A of the cardiac structure 604A. Blood generally exhibits a distinctly lower voltage than what is sensed on the surface (e.g., the endocardium) of the cardiac structure 604A. Since the voltage measured in blood generally is distinctly lower than the voltage measured on the surface of the cardiac structure 604A, there may be a steep gradient between the two values of the sensed voltage (i.e., the values of the metric at the sensed point 606A and the test point 610A). If the gradient exceeds a threshold, it may be determined that the sensed point 606A is located within a threshold distance of the surface of the cardiac structure 604A.

Referring to FIG. 6B, the electrode 602B, in this embodiment, is contacting the cardiac structure 604B, but is also pushing against the cardiac structure 604B and distorting it. Accordingly, a generated anatomical shell based on a signal sensed by a mapping electrode 602B having this type of contact with the cardiac structure 604B will produce an anatomical shell that is larger than the actual shape of the cardiac structure 604B at the sensed point 606B. In other words, the sensed point 606B may not be an appropriate point to be intersected by the surface 604B. To determine whether the generated anatomical shell is a distorted shape of the actual shape of the cardiac structure 604B at sensed point 606B, a test may be performed, using a metric as discussed above, with respect to a test point 610B.

In embodiments, a determination may be made as to whether the electrode 602B is touching the surface of the cardiac structure 604B. That is, since the electrode 602B is touching the surface of the cardiac structure 604B, a voltage will be sensed at the sensed point 606B that is distinctly higher than if the sensed point 606B were sensing a voltage in the blood pool 608B. Accordingly, it can be determined that the electrode 602B is touching the surface of the cardiac structure 604B. Additionally, or alternatively, a force-sensing metric, an impedance metric, and/or the like, may be utilized to determine whether the electrode 602B is contacting the surface of the cardiac structure 604B. In embodiments, after making this determination, the test may be performed.

In particular, a test point 610B may be selected that is located within a test neighborhood of sensed point 606B. Since the sensed point 606B is one of an outermost point sensed by the mapping probe, the selected point will be located below the surface of the cardiac structure 604B with respect to the sensed point 606B. Since the sensed point 606B is distending the surface of the cardiac structure 604B, a test point 610B and a corresponding voltage may, for example, have been sensed that is just touching the surface of the cardiac structure 604B (similar to the configuration shown in FIG. 6A) and is not distending the surface of the cardiac structure 604B, assuming a suitable density of signals were sensed by the mapping probe. Accordingly, the test point 610B may have a voltage similar to the voltage of the sensed point 606B and the gradient for the two values might not exceed a threshold. In this example, the test point 610B may be replaced with the sensed point 606B in the set of points that the surface of the anatomical shell intersects since the gradient does not exceed a threshold and since the sensed point 606B is touching the surface of the cardiac structure 604B, as determined by the voltage sensed at the sensed point 606B. By replacing the sensed point 606B with the test point 610B, the anatomical shell may more accurately represent the actual shape of the cardiac structure 604B.

Referring to FIG. 6C, the electrode 602C in this embodiment is not contacting the cardiac structure 604C. Accordingly, a generated anatomical shell based on a signal sensed by a mapping electrode 602C having this type of contact with a cardiac structure 604C may produce an anatomical shell that is smaller than the actual shape of the cardiac structure 604C at this sensed point 606C. To determine whether the generated anatomical shell is a distorted shape of the actual shape of the cardiac structure 604C at sensed point 606C, a test may be performed, using a metric as described above, with respect to a test point 610C.

In some embodiments, before performing the test, a determination as to whether the electrode 602C is touching the surface of the cardiac structure 604C may be performed. That is, since the electrode 602C is located in a blood pool 608C and not touching the surface of the cardiac structure 604C, a voltage may be sensed at the sensed point 606C that is distinctly smaller than if the sensed point 606C were touching the surface of the cardiac structure 604C. Additionally, or alternatively, a force-sensing metric, an impedance metric, and/or the like, may be utilized to determine whether the electrode 602C is contacting the surface of the cardiac structure 604C. Accordingly, it may be determined that the electrode 602C is not touching the surface of the cardiac structure 604C. In embodiments, when a determination is made that the electrode 606C is not touching the cardiac structure 604C, the test may not be performed. Instead, a physician or other medical professional may choose to map the cardiac structure 604C near sensed point 606C more thoroughly. In embodiments, if the test is performed, it may be determined that the sensed point 606C is not on the surface of the cardiac structure 604C since the voltage at a test point 610B, in the blood pool, will be similar to the voltage at the sensed point 606C and, therefore, the gradient of the metric will be low and not exceed a threshold.

In embodiments, the processing device 32 may be configured to automatically improve the accuracy of its algorithms by using one or more artificial intelligence (i.e., machine-learning) techniques, classifiers, and/or the like. In embodiments, for example, the processing device may use one or more supervised and/or unsupervised techniques such as, for example, support vector machines (SVMs), k-nearest neighbor techniques, artificial neural networks, and/or the like. In embodiments, classifiers may be trained and/or adapted using feedback information from a user, other metrics, and/or the like.

Figure 7:
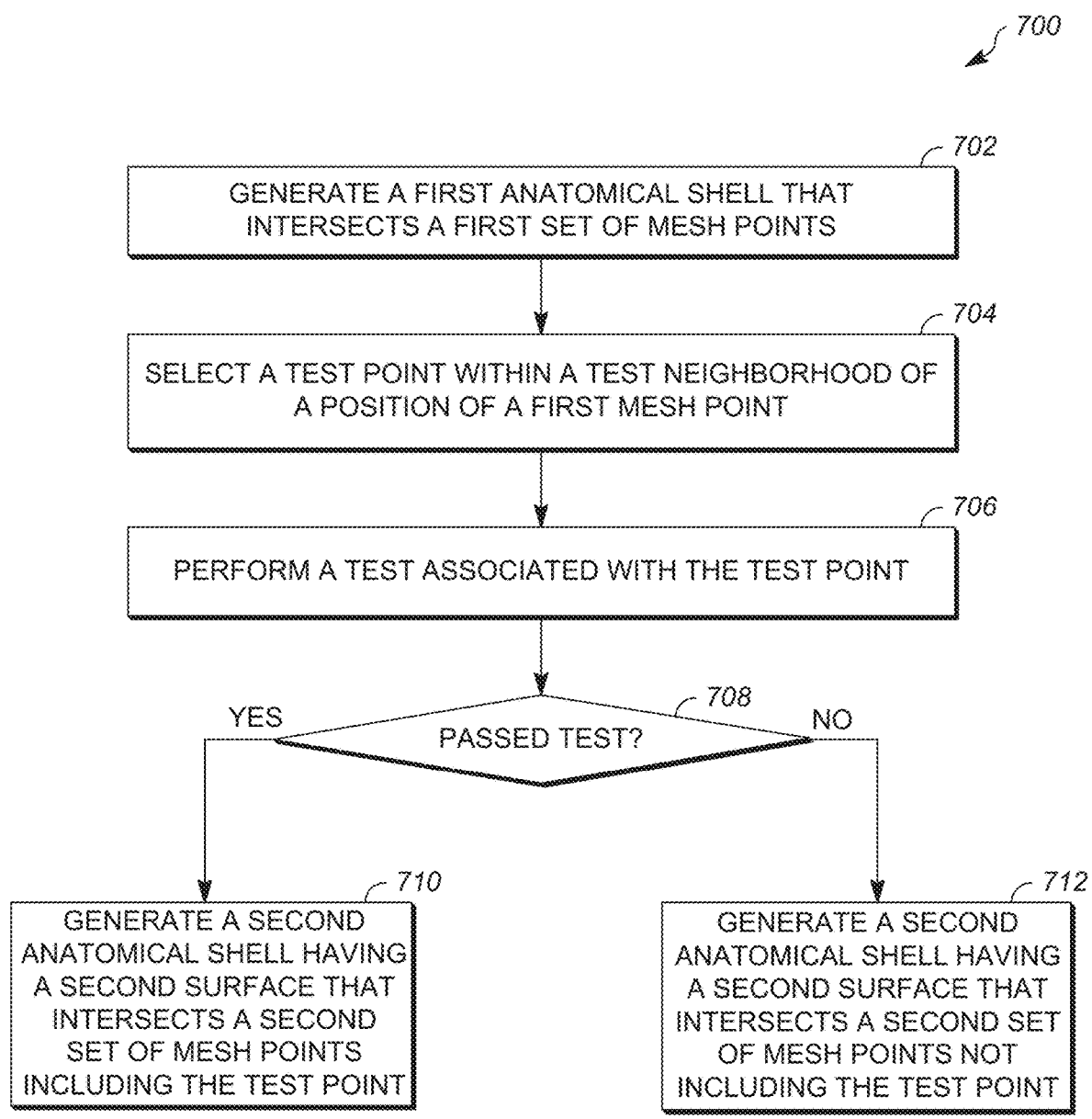
FIG. 7 is a flow diagram depicting another illustrative processor-implemented method for anatomical shell editing, in accordance with embodiments of the disclosure.

FIG. 7 is a flow diagram of a processor-based method 700 for adjustable depth anatomical shell editing, in accordance with embodiments of the disclosure. Embodiments of the method 700 may be performed, in whole or in part, by a mapping system (e.g., the mapping system 100 depicted in FIG. 1), which may include a processing device (e.g., the processing device 32 depicted in FIG. 1). As stated above, in embodiments, a generated anatomical shell may include points and/or sections that do not accurately represent the actual shape of the endocardium surface of the cardiac tissue from which the anatomical shell is generated. Embodiments of the method 700 may facilitate determining whether various points and/or sections of a generated anatomical shell are an accurate representation of the actual shape of the cardiac tissue that is being mapped. Embodiments of the method 700 use electrical data associated with various points intersected by a mesh (and, e.g., the surface of the anatomical shell), and electrical data from test points below the surface of the anatomical shell (e.g., points that are not intersected by the mesh) to determine whether the surface of the anatomical shell should, to more accurately represent a map of the cardiac tissue, intersect one or more of the test points instead of one or more of the mesh points.

As shown in FIG. 7, the method 700 includes generating a first anatomical shell, where the first anatomical shell comprises a first surface that intersects a first set of mesh points, the first set of mesh points corresponding to a number of signals, where each of the signals includes at least one respective sensed electrical signal (block 702). In embodiments, the signals corresponding to the first set of mesh points, may be sensed using a mapping probe that has the same, or similar, characteristics to the mapping probe 14 described above. Each mesh point has a respective set of position coordinates, as described above in FIG. 3. In embodiments, a mesh point of the first set of mesh points can be either a point in space or a voxel. The first surface of the first anatomical shell may be fitted to the first set of mesh points at the respective position coordinates of the mesh points. In embodiments, the first set of mesh points is a subset of all of the points corresponding to signals sensed by the mapping probe. At least some of the points sensed by the mapping probe that are not included in the first plurality of mesh points may be used as test points, as described below.

The method 700 also includes selecting a test point, where the first surface does not intersect the test point (block 704). As stated above, the method 700 may be used to determine whether a surface of a generated anatomical shell should intersect a first mesh point of the first set of mesh points or whether the surface should, instead, intersect another point, e.g., a test point. As such, in embodiments, the selection of a test point may be based on the first mesh point. That is, in embodiments, the test point may be selected based on whether the position of the test point is located within a test neighborhood of a position of the first mesh point. The test neighborhood, in embodiments, may be a sphere with its center located at the position of the first mesh point and may have some predetermined, selectable, and/or adjustable radius (e.g., 2 millimeters).

The position of the test point may be located below the endocardium surface of the first generated anatomical shell. In embodiments, a test point may be selected that has a position located in the opposite direction of the normal to the surface of the mesh at the first mesh point. In embodiments, the test point may have a position that is located closest to the position of the first mesh point of all the points sensed by the mapping probe that are located in the opposite direction of the normal. In this manner, for example, if the generated first anatomical shell intersects the outermost points sensed by the mapping probe and it is determined that the surface of the anatomical shell should intersect a test point instead of the first mesh point, the surface of the anatomical shell will be adjusted inward to intersect the test point.

To determine if a generated anatomical shell should intersect the test point instead of the first mesh point, the method 700 includes performing a test associated with the test point (block 706). In embodiments, the test may include multiple steps, such as, for example, embodiments of the steps discussed below with regard to FIG. 8 and/or above, with regard to FIGS. 6A-6C. Any number of other tests, algorithms, machine-learning techniques, and/or the like may be used to determine whether a mesh should be adjusted to intersect a test point.

After the test associated with the test point is performed, the method 700 includes determining whether the test was passed (block 708). If the test was passed, the method 700 includes generating a second anatomical shell that includes a second surface that intersects a second set of mesh points, where the second set of mesh points includes the test point (block 710). In embodiments, the test point may be substituted in place of the first mesh point. Additionally, in embodiments, the system may perform an interpolation and/or other smoothing technique to smooth the surface around the location of the test point. In embodiments, the method 700 may be performed with respect to other mesh points included in the first set of mesh points. If, on the other hand, the test was not passed, the method 700 includes generating a second anatomical shell having a second surface that intersects a second set of mesh points, where the second set of mesh points does not include the test point (block 712). In embodiments, the first mesh point may be included in the second set of mesh points. For example, the second set of mesh points, in this case, may be identical to the first set of mesh points.

Figure 8:
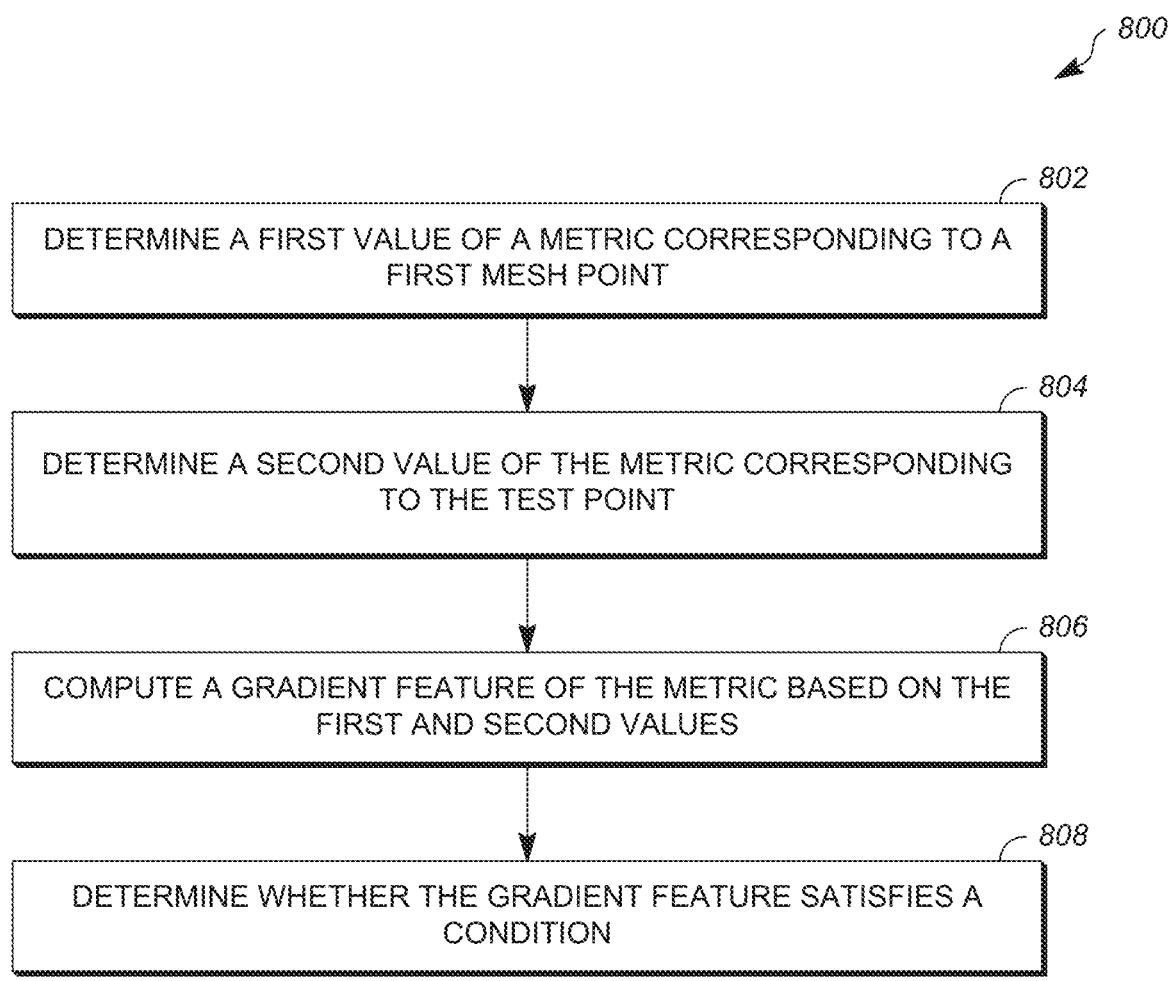
FIG. 8 is a flow diagram depicting an illustrative processor-implemented method for performing a test associated with a test point, in accordance with embodiments of the disclosure.

As stated above, FIG. 8 is a flow diagram depicting an illustrative processor-implemented method 800 for performing a test associated with a test point, in accordance with embodiments of the disclosure. The method 800 includes determining a first value of a metric corresponding to the first mesh point (block 802). The determined first value of the metric may be a magnitude of the metric at the first mesh point. For example, in embodiments, the first value of the metric can be the magnitude of the at least one respective sensed electrical signal corresponding to the mesh point. The method 800 also includes determining a second value of the metric corresponding to the test point (block 804).

As shown in FIG. 8, the method 800 also includes computing a gradient feature of the metric based on the first and second values (block 806). In embodiments, the gradient feature may be the difference of the first and second values, divided by the distance between the first mesh point and the test point. Embodiments, of the method 800 also include determining whether the gradient feature satisfies a condition. In embodiments, the condition may be satisfied when an absolute value of the gradient feature exceeds a threshold, where a value of the gradient is lower than a negative threshold, and/or the like.

For example, in embodiments, the test may include selecting a step size, s, which may be, for example, some distance (e.g., 0.1 mm, 0.2 mm, 1 mm, etc.). Then, for each mesh vertex position x, with normal n, embodiments of the method 800 may include evaluating the metric, f, for x and x-sn. In embodiments, the anatomical shell may be generated by interpolating signal features collected in a grid to the mesh surface, in which case, the evaluation may be grid-based, and may be performed as described in more detail below, with respect to grid-based tests. In embodiments, the evaluation may be mesh-based, such as, for example, a distance-weighted average of the neighborhood within some radius, r, (e.g., 2 mm). The method 800 may include computing the gradient feature:

$$G = \frac{f(x) - f(x - sn)}{s}$$

Where, if $G < -G_m$ (where $-G_m$ is some negative threshold), the method 800 may include repositioning the vertex at x-sn, and repeating the process at that vertex. Otherwise, a new vertex may be chosen, and the test applied with respect to that new vertex.

As indicated above, some mapping systems may utilize a grid-based data aggregation scheme. In such systems, for each collected electrode/spatial record, embodiments may include establishing a pre-determined radius of influence, such that the metric is assigned to a set of surrounding voxels. If a voxel is influenced by more than one electrode acquisition, embodiments may include averaging the measurements. This may be based on a philosophy that tissue shape and position don't necessarily change over time, and, consequently, that it may be assumed that all measurements should be considered, not just the latest or first one.

In embodiments, for each voxel, $v_i$, with assigned valid metrics for itself and its neighbors, the test may include computing the cross-voxel gradient:

$$G(v_i) = \frac{f(v_i) - f(v_c)}{d}$$

where $v_c$ is the facing voxel and d is the distance. The test may further include finding $$G_M = \max\{G(v_i)\}$$

which is the voxel's processed metric value. Where data density is sufficient, this measurement may provide a good indication of the voxel's position on the gradient curve, and consequently, any generated mesh triangle. In embodiments, the system may also, or alternatively, consider the direction of maximum gradient, which may be expressed, for example, as a vector formed between the two adjacent voxels.

Based on the above metric value assignment, any number of refinement steps can be taken. In embodiments, the refinement steps may be based on a threshold, which may be variable or fixed, predetermined, adjustable, selectable, and/or the like. For example, in embodiments, voxels with low values may be simply turned off. In embodiments, an entire other surface can be generated using our existing mesh generation algorithm (with the iso level being applied as a normalized threshold to a normalized grid), shown along with the standard reconstruction, with the user choosing which areas of the reconstruction to snap to the new surface In embodiments, a direct visualization of some form of the metric as it's acquired can be used to indicate instantaneous proximity to cardiac tissue (for example, an averaging of currently sensed out-of-cardiac-band impedance values). In some instances, however, such embodiments may have some flaws because, for example, any given set of instantaneous measurements may be distorted by noise and/or other ambient signals near the probe for some metrics (application of ablation energy, for example, is the cause for many such effects). As such, in embodiments, the refined anatomical shell may utilize an aggregation of one or more of the above metrics over time and space, allowing for handling of such outliers, resulting in an accurate approximation of the cardiac tissue's shape and position. Utilizing the aggregation of one or more of the above metrics over time and space, in conjunction with the acquired positions of the probe, which are generally considered stable and reliable, an alternative indication of proximity to cardiac tissue can be generated by computing the proximity to the refined anatomical shell. Embodiments may use this alternative indication of proximity to cardiac tissue to overcome the above challenges (i.e., distortion caused by noise and/or other ambient signals near the probe) by itself or in conjunction with other methods by deciding to make a switch when noise and/or ambient signals are detected (for example, by detecting that ablation energy is being applied, or by sensing heightened levels of noise on the acquired mapping probe signal).

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A system comprising:
a mapping probe configured to sense a plurality of signals associated with a cardiac structure;
a processor configured to:
generate a first anatomical shell, wherein the first anatomical shell comprises a first surface that intersects a first plurality of mesh points, the first plurality of mesh points corresponding to a plurality of signals, wherein each of the plurality of signals includes at least one respective sensed electrical signal; and
perform a test, wherein to perform the test, the processor is configured to:
select a test point, wherein the first surface does not intersect the test point, the test point having a position within a test neighborhood of a position of a first mesh point of the first plurality of mesh points;
determine a first value of a metric corresponding to the first mesh point;
determine a second value of the metric corresponding to the test point;
compute a gradient feature of the metric based on a difference between the first value of the metric corresponding to the first mesh point and the second value of the metric corresponding to the test point;
determine whether an absolute value of the gradient feature exceeds a gradient threshold; and
generate a second anatomical shell, wherein the second anatomical shell comprises a second surface that intersects a second plurality of mesh points, wherein if the absolute value of the gradient feature exceeds the gradient threshold, the second plurality of mesh points includes the test point, and if the absolute value of the gradient feature does not exceed the gradient threshold, the second plurality of mesh points does not include the test point; and
a display device configured to display the second anatomical shell.

2. The system of claim 1, wherein the processor is configured to:
select an additional test point when the absolute value of the gradient feature does not exceed the gradient threshold, the additional test point having a position within the test neighborhood of the position of the first mesh point; and
perform the test using the additional test point for the test point.

3. The system of claim 1, wherein the position of the test point is located opposite the direction of a normal to the first surface at the first mesh point.

4. The system of claim 1, wherein the test neighborhood comprises a sphere with a radius of 2 millimeters.

5. The system of claim 1, wherein the metric comprises at least one of an out-of-cardiac-band impedance measurement, a unipolar electrode activation voltage measurement, a contact force measurement of the mapping probe, and a position-based cardiac motion measurement.

6. The system of claim 1, wherein to perform the test, the processor is further configured to:
determine a sensed voltage value corresponding to the test point; and
determine whether the sensed voltage value exceeds a voltage threshold.

7. The system of claim 6, wherein the processor is configured to:

include the test point in the second plurality of mesh points when the sensed voltage value exceeds the voltage threshold; and not include the test point in the second plurality of mesh points when the sensed voltage value does not exceed the voltage threshold.

8. A processor-based method for anatomical shell editing, the method comprising:

generating a first anatomical shell, wherein the first anatomical shell comprises a first surface that intersects a first plurality of mesh points, the first plurality of points corresponding to a plurality of signals, wherein each of the plurality of signals includes at least one respective sensed electrical signal;

selecting a test point, wherein the first surface does not intersect the test point, the test point having a position within a test neighborhood of a position of a first mesh point;

performing a test associated with the test point, comprising:

determining a first value of a metric corresponding to the first mesh point;

determining a second value of the metric corresponding to the test point;

computing a gradient feature of the metric based on a difference between the first value of the metric corresponding to the first mesh point and the second value of the metric corresponding to the test point; and determining whether the gradient feature exceeds a gradient threshold; and generating a second anatomical shell, wherein the second anatomical shell comprises a second surface that intersects a second plurality of mesh points, wherein:

if the gradient feature exceeds the gradient threshold, the second plurality of mesh points includes the test point; and if the gradient feature does not exceed the gradient threshold, the second plurality of mesh points does not include the test point.

9. The method of claim 8, wherein, if the gradient feature does not satisfy the condition, the method further comprising:

selecting an additional test point, the additional test point having a position within the test neighborhood of the position of the first mesh points; and performing the test associated with the additional test point.

10. The method of claim 8, wherein the position of the test point is located opposite the direction of a normal to the first surface at the first mesh point.

11. The method of claim 8, wherein performing the test further comprises:

determining a sensed voltage value corresponding to the test point; and determining whether the sensed voltage value exceeds a voltage threshold.

12. The method according to claim 11, wherein:

if the sensed voltage value exceeds the voltage threshold, the second plurality of mesh points includes the test point; and if the sensed voltage value does not exceed the voltage threshold, the second plurality of mesh points does not include the test point.

* * * * *